(12) United States Patent
Mattiuzzi et al.

(10) Patent No.: US 8,345,940 B2
(45) Date of Patent: Jan. 1, 2013

(54) METHOD AND SYSTEM FOR AUTOMATIC PROCESSING AND EVALUATION OF IMAGES, PARTICULARLY DIAGNOSTIC IMAGES

(75) Inventors: Marco Mattiuzzi, Grassina Bagno a Ripoli (IT); Toni Werner Vomweg, Neuwied (DE)

(73) Assignee: Bracco Imaging S.P.A., Milan (IT)

( * ) Notice: Subject to any disclaimer, the term of this patent is extended or adjusted under 35 U.S.C. 154(b) by 1229 days.

(21) Appl. No.: 12/089,911

(22) PCT Filed: Oct. 24, 2006

(86) PCT No.: PCT/EP2006/067729
§ 371 (c)(1),
(2), (4) Date: Jun. 20, 2008

(87) PCT Pub. No.: WO2007/048797
PCT Pub. Date: May 3, 2007

(65) Prior Publication Data
US 2011/0176710 A1    Jul. 21, 2011

(30) Foreign Application Priority Data
Oct. 25, 2005  (EP) .................................... 05425751

(51) Int. Cl.
*G06K 9/00*    (2006.01)
(52) U.S. Cl. ..................................................... 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | |
|---|---|---|
| 6,430,430 B1 | 8/2002 | Gosce |
| 6,738,499 B1 | 5/2004 | Doi et al. |
| 2011/0268338 A1* | 11/2011 | Collins et al. ................. 382/131 |

OTHER PUBLICATIONS

Vomweg T W et al: "Improved artificial neural networks in prediction of malignancy of lesions in contrast-enhanced MR-mammography," Medical Physics, AIP, Melville, NY, US, vol. 30, No. 9, Sep. 2003, pp. 2350-2359, XP012012221, ISSN: 0094-2405, the whole document.

(Continued)

*Primary Examiner* — Atiba O Fitzpatrick
(74) *Attorney, Agent, or Firm* — Themis Law

(57) ABSTRACT

Method for automatic processing and evaluation of images, particularly diagnostic images, comprising an image processing tool in the form of a software program which is executable by the computer hardware and which image processing tool processes image data of a digital input image generating a modified digital output image whose image data are outputted in a graphical and/or alphanumerical format highlighting certain predetermined features or qualities of the corresponding regions of an imaged body or object, characterized in that the image processing tool comprises a first image detecting module which is an image processing module based on image processing non expert algorithms and which furnishes at its output a modified image file which modified image data are further processed by a classification or evaluation module which is a second image processing module comprising an image processing tool consisting in an expert image processing algorithm such as a classification or prediction algorithm the output of which is a further modified image file in which the pixels or voxels are highlighted corresponding to imaged object having a predetermined feature or quality.

24 Claims, 20 Drawing Sheets

OTHER PUBLICATIONS

Nattkemper T W et al: "Tumor feature visualization with unsupervised learning" Medical Image Analysis, Oxford University Press, Oxofrd, GB, vol. 9, No. 4, Aug. 2005, pp. 344-351, XP004947779, ISSN: 1361-8415, Abstract; Figs. 1, 4, pp. 344-346, left-hand column, paragraph 2.

Sokol R J et al: "Morphometry of Blood Monocytes in Malignant Lymphoma," Journal of Clinical Pathology (London), vol. 38, No. 8, 1985, pp. 904-907, XP002369937, ISSN: 0021-9746, Abstract.

Chiou Y S P et al: "Neural-knowledge base object detection in Hybrid Lung Nodule Detection (HLND) system," Neural Networks, 1994. IEEE World Congress on Computational Intelligence., 1994 IEEE International Conference on Orlando, FL, USA Jun. 27-Jul. 2, 1994, New York, NY, USA, IEEE, vol. 7, Jun. 27, 1994, pp. 4180-4185, XP010128047, ISBN: 0-7803-1901-X, Abstract.

Vomweg Toni W et al: "Combination of low and high resolution sequences in two orientations for dynamic contrast-enhanced MRI of the breast: more than a compromise," European Radiology. Oct. 2004, vol. 14, No. 10, Oct. 2004, pp. 1732-1742, XP002369938, ISSN: 0938-7994.

* cited by examiner

OBJECT 1

Step 1: find maximum intensity

Step 2: seeding with individual threshold

Object 1

OBJECT 2

Step 3: find second highest intensity

Second highest intensity

Step 4: seeding with individual threshold

Object 2

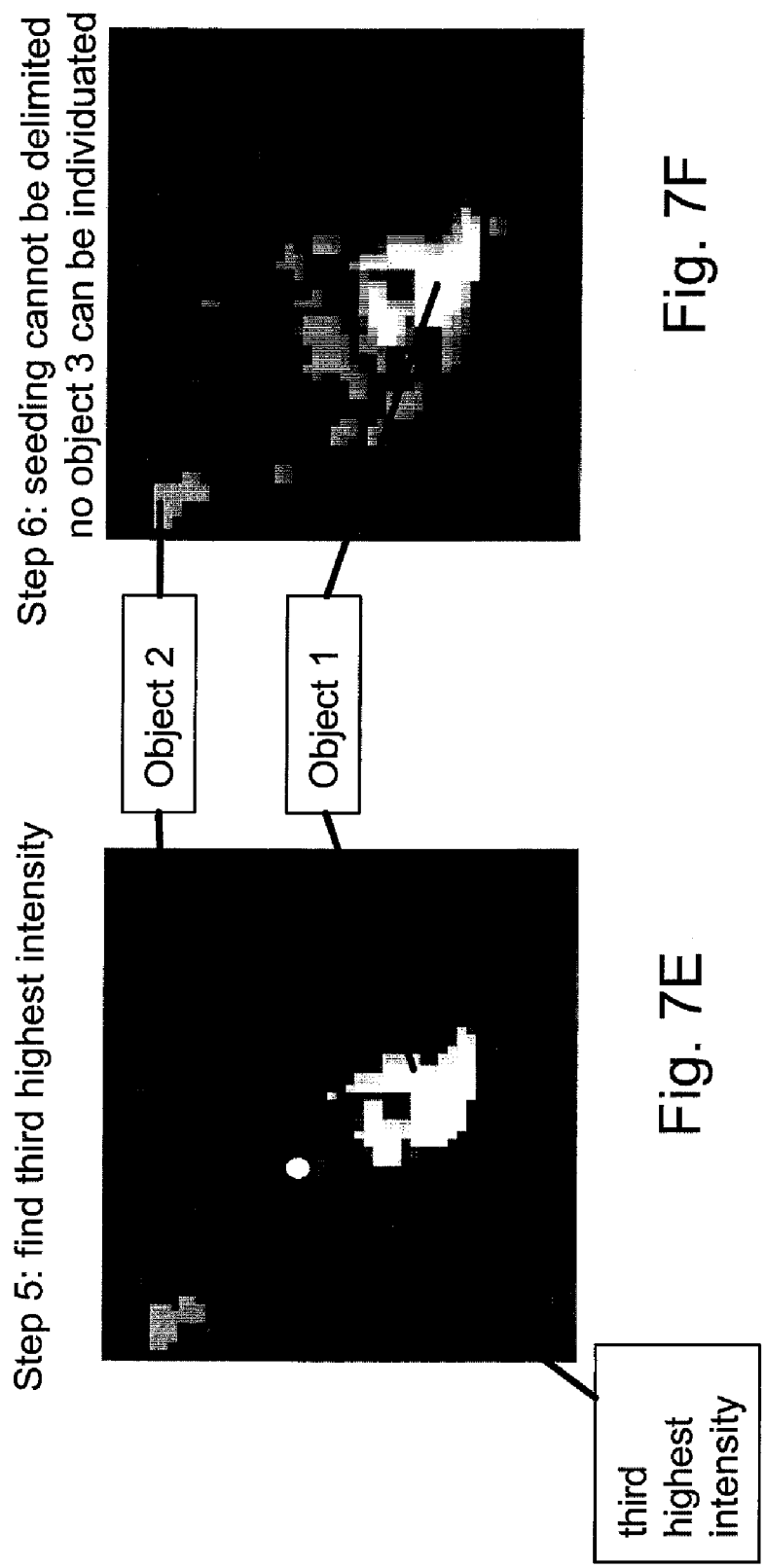

Proportion
- Lesion size (mm³)
- Maximum diameter (mm)
- Minimum diameter (mm)

Compactness
- Quotient surface/volume
- Fractal dimension

—    0.0 D    1.0 D    2.0 D    3.0 D    2.4 D

Bubbles
- Size of all bubbles (mm³)
- Count of bubbles
- Size of biggest bubble (mm³)

Homogeneity
- Average signal intensity
- Signal intensity deviation
- Margin characteristic
- · · ·

| Parameter | Formula | Explanation |
|---|---|---|
| ENH1 | (SI 1−SI 0)/SI 0 | Relative enhancement from preCM to postCM1 |
| ENH2 | (SI 2−SI 0)/SI 0 | Relative enhancement from preCM to postCM2 |
| ENH3 | (SI 3−SI 0)/SI 0 | Relative enhancement from preCM to postCM3 |
| ENH4 | (SI 4−SI 0)/SI 0 | Relative enhancement from preCM to postCM4 |
| ENH5 | (SI 5−SI 0)/SI 0 | Relative enhancement from preCM to postCM5 |
| ENHmax | Max (ENH1, ENH2, ENH3, ENH4, ENH5) | Peak value among ENH1, ENH2, ENH3, ENH4, ENH5 |
| ENHalt | Max (ENH1, ENH2) | Peak value among ENH1 and ENH2 |
| ENH 1−2 | ENH2−ENH1 | Relative signal increase between the first and the second postcontrast measurement |
| MSLP | Max (ENH1, ENH 1−2) | Maximum slope: relative signal increase from preCM to CM1 or from CM1 to CM2, whichever value is higher |
| SAT | $(SI1)/SI_{max}$ | Saturation: the signal intensity reached during CM1 with respect to the peak signal intensity reached after CM |
| ENH2−5 | ENH2−ENH5 | Washout parameter indicating the change of signal intensity from CM2 to CM5 |
| ENH3−5 | ENH3−ENH5 | Washout parameter indicating the change of signal intensity from CM3 to CM5 |

Fig. 14

| Name | Testwoman | Investigation | Dynamic MRI Breast |
|---|---|---|---|
| Surname | Birgit | Date of MRI | 11.02.2004 |
| Birthdate | 01.01.1945 | Date of Evaluation | 11.02.2004 |

| | | | |
|---|---|---|---|
| Protocol name: | Mainz special | # of series detected: | 15 |
| Orientation: | coronal, transversal | T2w series analyzed: | 2, 3, 4 |
| | | T1w series analyzed: | (5), 7, 8, 9, 10 |
| Contrast Media: | applied | CM applied after series | 6 (20s break) |
| Registration: | applied coronal | Registered series: | (5), 7, 8, 9, 10 |
| | applied transversal | Registered series: | (5), 11 |
| Registered series: | stored (LOCAL) | Series stored: | 7, 8, 9, 10, 11 |
| CADMRM version: | 0.1b-20031231 | ANN version: | D001-20031231-30 |

| # of detected lesions | 1 | Overall assessment: | highly suspicious |
|---|---|---|---|

| Lesion # | 1 | Position breast | left |
|---|---|---|---|
| Slice # t1w coronal | 35 | Quadrant | inner lower quadrant |

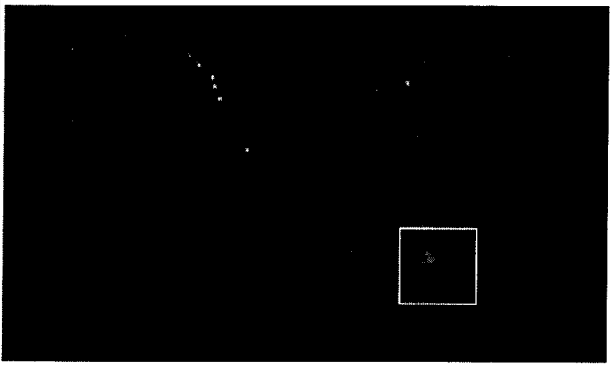

Zoom:

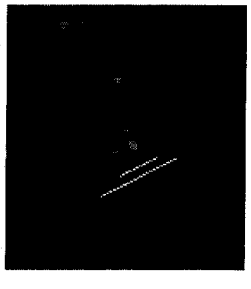

Size overall: 9 mm
Size core: 5 mm

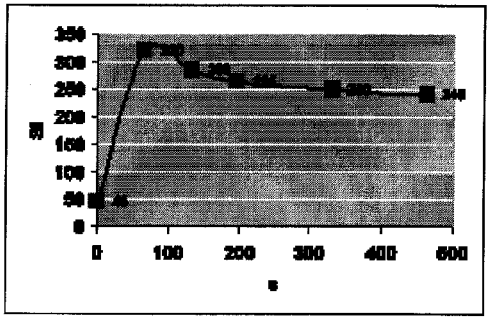

Morphology:
  Form                      spiculated
  Internal                  heterogeneous → rim
  Border                    NA (core to small)
Dynamic
  Maximum after s           72s (after CM injection)
  Initial Enhancement       585.7%
  Saturation ENH1           100%
  Washout                   25.0%
Artificial Neural Network
  Likelihood of Cancer      93.7 %
                            highly suspicious
Error possibility           10.4%

Fig. 20

METHOD AND SYSTEM FOR AUTOMATIC PROCESSING AND EVALUATION OF IMAGES, PARTICULARLY DIAGNOSTIC IMAGES

The invention relates to a method for automatic processing and evaluation of images, particularly diagnostic images, comprising an image processing tool in the form of a software program which is executable by the computer hardware and which image processing tool processes image data of a digital input image generating a modified digital output image whose image data are outputted in a graphical and/or alpha-numerical format highlighting certain predetermined features or qualities of the corresponding regions of an imaged body or object.

Image processing and particularly diagnostic image processing is an important item of the present days. Non invasive and slightly invasive imaging techniques and devices have been subject to important improvements and are able to furnish highly reliable and precise diagnostic images of selected anatomical district of patients. The improvements in diagnostic image acquisitions have lead to a reduction of artefacts and to high contrast and high resolution images. So diagnostic images potentially comprise a high rate of information about the features of the imaged anatomical districts and tissues. Nevertheless if such an image is printed or visualized on a monitor, the direct visual detection of lesions or of searched particular features or qualities of the imaged tissues as well as the individuation and evaluation of imaged objects like lesions or similar is not simple and is still very dependent on the personal skill and experience of the persons interpreting the image.

Furthermore the different imaging techniques are able to detect and highlight different features or qualities of an imaged object as a particular tissue kind or a lesion due to the particular way with which the different tissue kinds interacts with the physical means applied for acquiring the image by a certain imaging technique. So, in order to detect lesions or to establish the existence of certain features or qualities of the imaged tissue, often images of the same body or object are acquired using different imaging techniques and the tissue kind or the searched features or qualities are analysed by comparison or consideration of images acquired with the said different techniques. This comparison is often not so simple and rapid when it is done by direct visual analysis and interpretation, since the information of each image identified separately has to be correlated with the information obtained by the analysis of other images.

A considerable amount of time is spent in interpreting the acquired images as compared to the time needed for the acquisition of such images.

Furthermore, due to the importance of early detection of lesions, particularly related to tumour tissues, when the human interpreter has a doubt about the fact if a region of the image which has been visually identified corresponds to such a lesion, this region is normally considered a lesion and the corresponding region or tissue of the imaged body is subjected to a further and deeper diagnostic analysis such as biopsy or other particular techniques. Generally this kind of region of the images are defined as false positives, i.e. as images of a region of an imaged body which appearance on the image corresponds at least partially or is very similar to the appearance of a real lesion in the imaged body, but which region of the imaged body is in reality not a lesion.

False positives are a big problem since for security sake they will be subjected in any case to further investigation determining an increase of costs and time.

In order to help the interpretation of the diagnostic images and to reduce at least partially the rate of false positives in the lesion detection or in the recognition of searched features or qualities of the imaged body several different image processing tools has been developed.

This tools can be divided in two main classes, Non expert and Expert image processing tools respectively.

Non expert image processing tools operate blindly on the imaged data consisting in the variables which define the pixel appearance and which are determined univocally for each pixel or voxel by the image acquisition method and device from the interaction of the physical image acquisition means with the imaged body, for example from the interaction of X-rays or electromagnetic pulses emitted and/or transmitted and/or reflected by the imaged object depending on the kind of imaging techniques that is applied. The information used for the processing consists of parameters defining the appearance of the pixels or voxels of the image and eventually also of the pixels or voxels comprised in a certain surroundings of each pixel or voxel of the image. Also the information relating to the topographical or topological relation between the pixels of the acquired image is used.

The above defined non expert tools are based on mathematical operators having a well defined structure.

This kind of tools are very efficient in somehow filtering the image by sorting out the pixels which do not represent probable lesions or regions of the imaged body having a certain searched feature or quality. As a result these processing tools generally generate a modified image in which the pixels are highlighted whose appearance corresponds to the interaction of a lesion or of regions of the imaged body having the searched features or qualities with the physical means for acquiring the image. It is important to stress out that the sorting out operated by these kind of image processing tools is based on criteria which are implicit to the appearance of the lesion or of the searched feature or quality in an image obtained by a certain techniques and determined by the interaction properties of the lesion or feature or quality and its physical effects on the physical means used in the image acquisition technique. For example a tumour tissue in which contrast media is present will reflect ultrasound beams with a higher intensity than the surrounding tissue so that the variable determining the pixel appearance corresponding to the image of the said tumour tissue in a grey scale image will correspond to a high intensity level of the reflected beam and to a white appearance or brighter appearance of the pixel with respect to the pixels relating to regions where the tumour tissue is not present.

Further tools falling within the class of non expert image processing tools are algorithm used to correct images in relation to movement artifacts caused by the imaged body during the imaging session. These algorithms are particularly relevant for the detection of dynamic features of the body region being imaged.

Non expert tools are generally not able to differentiate objects whose appearance in the image is similar due to their similar way of interaction with the physical nature of the image acquisition process as for example malignant and benign tumour lesions. They simply indicate more clearly the pixels in the image which corresponds to regions of the imaged body which has interacted with the physical means for acquiring image information in the way it is expected by the region of the imaged object having the searched features or qualities.

This results furnished by non expert tools needs further interpretation for decision making with reference to the characteristics of the imaged objects.

Expert image processing tools operates on a different approach. These tools can be based on classification algorithms which are able to be charged with knowledge so that this tools simulate expert knowledge. Expert tools do not operate by means of rigid rules describing the knowledge of the skilled person but relating to the present application to images, these expert tools carry out a decision making process in the unmodified image. This is different from non expert tools which examine a modified image and which determine the presence of certain feature basing on fixed rules of evaluation. The basic mathematical structure of the algorithm of expert tools in the meaning of the present invention, is capable to be transformed in any kind of functional relation by means of a training process in which the relevant knowledge for providing decisions is charged in the mathematical structure. These kind of tools operate with a very high non linear approximation of functional relationships between input data and output data. Operating with these tools requests an analysis of the problem and the parameterisation of the relevant input and output variables in order to generate a training database which can be mathematically handled by the mathematical structure of the algorithm for implementing the knowledge in it. Typical algorithms used for classification are Artificial Neural Networks, Clustering algorithm and similar.

Classification algorithms are able to predict or decide relating to the classification of a pixel or voxel of an image relating to the fact if these pixels represent an imaged region corresponding to a lesion or to the searched feature or quality by considering the experience. This experience consists in the training database. This training database is a collection of images of objects of which is known that one or more region of the said objects have or do not have the searched features or qualities. In a very simplified model the operation of the classification algorithm could be interpreted as a sort of pixel by pixel comparison of the image under examination with the images of the training database in order to determine if the said image under examination or some of its pixels could be related to the quality which corresponds to the pixels in the images of the training database having identical or similar appearance. Thus this kind of algorithms and the methods and systems for image processing using the said algorithms do not simply highlight pixels in an image in order to emphasize its physical appearance which is related to the features or qualities of the corresponding region of the imaged body as the above mentioned non expert systems but it highlights pixels on the basis of the decision or prediction of the feature or quality of the corresponding region of the imaged body and this decision and prediction is taken basing on a sort of phenomenological experience which is given to the mathematical structure by means of known cases.

Summarizing the non expert image algorithms have the aim of helping in reading the image for detecting imaged objects which have a certain physical response to the means used for acquiring the image, while expert system do not care about the acquisition mechanism and give a prediction about a searched feature or quality of the object which has been imaged basing on an empirical experience.

Despite the fact that expert imaging tools are able to differentiate objects whose appearance in the image is similar due to their similar way of interaction with the physical nature of the image acquisition process as for example malignant and benign tumour tissue, also expert tools are currently affected by the problem of the so called false positives.

As an output the expert image processing tools furnishes a modified image in which the pixels corresponding to objects in the imaged body which are considered as having the searched features or qualities are highlighted and eventually also an alphanumerical report in which the statistical degree of reliance of each evaluation result of each object highlighted in the modified image.

Currently the two kinds of image processing tools namely expert and non expert tools are used separately and alternatively to each other providing for different systems for helping in the image interpretation particularly in the medical detection and/or diagnosis of tumour lesions or other kind of pathologies and both the two kinds of tools are affected by the problem of the so called false positives.

Further to the interpretation of single static images of a body which are directed to the detection and evaluation of pixels of the image relating to the feature or quality of the corresponding regions of the imaged body there exists also so called dynamic imaging techniques which are useful in detecting so called dynamic features of the imaged body or regions thereof.

An example of this kind of dynamic features derive from the signal intensity/time-curves of a contrast agent dynamics presented at a certain instant in the imaged object. This kind of investigation is particularly useful in relation with lesions which are connected with physiological effects such as an enhanced vascularisation of tumour tissues. Contrast media consists in substances delivered to the anatomical district to be imaged which substances has an especial way to interact with the physical imaging means and a special response which helps in differentiating their contribution to the image form the surrounding tissues of an imaged anatomical district. From a time sequence of images of the same anatomical district before delivering contrast media to the tissue and at certain time interval after contrast media administration it is possible to determine a certain number of different parameters which gives a measure of the speed of contrast media uptake and washout within the imaged region or in objects of the imaged region and even the dimension of the area in the imaged object in which diffuses the contrast media as well as other parameters which will be described with more details in the following description. The results of the investigation of the dynamic features and particularly the results of the investigation of the contrast media furnishes time dependent parameters which are visualized as so called signal intensity/time-curves.

This kind of technique is a separate one from the above mentioned and is currently used as a parallel investigation method. The results of the said dynamic features of the imaged object are than considered as separate information which is additional to the results of the above mentioned image processing tools. This combination is carried out by the person interpreting the images and is merely a comparison of the results obtained by the image processing tools for the evaluation or the detection of the features or qualities of the imaged objects with the results of the investigation of the dynamic features as explained above. Also in this case complete evaluation of the features or qualities of the imaged objects in the imaged body are dependent from the skill of the person which evaluates the output data of the image processing tools and of the dynamic features measuring tools and is time consuming and expensive.

It is important to stress out that the term image used in the description and in the claims has to be considered to comprise either two dimensional images such as an image corresponding to a slice of the imaged object according to a section plane of it or to a three-dimensional image or volumetric image. Two dimensional images are formed by arrays of pixels and three dimensional images by arrays of voxels. Each pixel or voxel has a precise position in the image space and its aspect is determined by parameters which value is determined by the values of the parameters which characterizes the physical signals used according to the chosen imaging technique for acquiring the image after that these physical signals have been subject to interaction with the body to be imaged or with a part of it.

Generally the significant parameter of the physical signal after interaction with the body to be imaged is the intensity of it; other parameters of these signals are used in order to generate a univocal correspondence with a dot or a point of the imaged body and a corresponding pixel or voxel in the image such that the topographical relation between pixels or voxels of the image represents the topographical relation between the different dots of the imaged body corresponding to the said pixels or voxels.

So it clearly appears that current image processing tools and the methods actuated by this tools operate at a pixel or voxel level and do not consider that the target of a diagnostic examination by imaging is the identification of objects having certain features or qualities.

A first object of the present invention is to provide an enhanced system for the automatic processing and evaluation of images, particularly diagnostic images which reduces the detection and indication of the so called false positives in the processed image.

A further object of the present invention is to generate a unique tool which is easier to use by the person evaluating an image by limiting his tasks to analyzing output data in conjunction with the image.

A further object of the present invention consists in the fact of increasing the output information of the image processing tool in order to further facilitate the last step of image interpretation process which is made by a person, particularly relating to recognising image zones which relates to objects of the imaged body which have interesting or searched features or quality such as generic tumour tissues or even benign and malign tumour tissues.

The present invention achieves the above mentioned aims by means of a method for automatic processing and evaluation of images, particularly diagnostic images, comprising an image processing tool in the form of a software program which is executable by the computer hardware and which image processing tool processes image data of a digital input image generating a modified digital output image whose image data output is generated in a graphical and/or alphanumerical format highlighting certain predetermined features or qualities of the corresponding regions of an imaged body or object and in which the image processing tool comprises a first image processing module based on image processing non expert algorithms which is defined herein as a detection module and which furnishes at its output a modified image file which modified image data are further processed by a second image processing module comprising an image processing tool consisting in an expert image processing algorithm such as a classification or prediction algorithm and which second image processing tool is defined herein as a classification module and the output of which is a further modified image file in which the pixels are highlighted corresponding to imaged object having a predetermined feature or quality.

The method of the present invention which consists in the combination of non expert and expert image processing tools has led to the a relevant reduction of false positives and to classification results which have a very high score in correctly determining the features or qualities searched for each pixel of the images.

Preprocessing image data by means of non expert image processing tools and using the output data of these on expert image processing tools as input data for a following processing step in which expert image processing tools such as classification tools are applied somehow has a synergic effect on the end results of image processing and evaluation. An explanation of this could lie in the fact that presumably there is a relation between the detection and classification of false positives by the non expert and expert image processing tools. This synergic effect is strong due to the completely different nature of investigation of the expert and non expert systems (as explained above) the logical expectations would have lead to the assumption that combining non expert and expert systems would not have lead to a significant reduction of the rate of incidence of false positives in the detection and evaluation results. Thus the skilled person logically analysing the problem of false positives and the different imaging tools currently known would not have considered the combination of expert and non expert system as a potentially valid solution of the problem.

As a further improvement the method according to the present invention also provides for a detection module which comprises a chain of different non expert image processing tools and the image data of the acquired image is processed by this chain, the output data of a previous image processing tool being used as input data of the following image processing tool.

A particular embodiment of the method according to the present invention provides a detection module comprising the following image processing tools a first segmentation tool which detects pixel cluster in the image which are labelled as an image object corresponding to an object in a region of the imaged body presumably having homogeneous features or qualities and a following morphological parameters detection tool which carries out an analysis of each image object individuated by the previous processing with the segmentation tool and labels part of the said object individuated in the image as valid or non valid relatively to the searched features or qualities by comparing the parameters describing the morphology of the said objects individuated in the image with the parameters describing the typical or nominal morphology of the image of objects having the searched features or qualities.

Relating to the subsystem for extracting dynamic features also this module of the image processing and evaluation method according to the invention consists in a chain of different non expert image processing tools and the image data of the acquired image is processed by this chain, the output data of a previous image processing tool being used as input data of the following image processing tool.

According to one particular embodiment the subsystem for extracting dynamic features comprises a first image registration tool which neutralises patients movements occurred during the imaging session where the sequence of time delayed images has been acquired. The results of these registration processing steps, namely the output data of the registration processing tool being further used as an input of a first segmentation tool which detects pixel cluster in the image which are labelled as an image object corresponding to an object in a region of the imaged body presumably having homogeneous features or qualities and a following morphing tool which carries out a shape analysis of each image object detected by the previous processing with the segmentation tool. Output data of the morphing tool are then used for carrying out the dynamic feature extraction of the imaged body.

According to a further feature of the present invention it is possible to combine the output data of the detection tool and of the dynamic feature extraction subsystem. The images obtained after the registration step of the sequence of images which is carried out by the subsystem for the dynamic feature extraction is further subjected to a segmentation step and the output image data of the segmentation step is used as image input data of the morphing tool of the detection module. Thus morphology information is retrieved form the image data also from the images of the sequence of images generally used for the dynamic feature extraction.

Static images, typically used for being processed by the detection module for extracting morphology information of the imaged objects are generally high resolution images. The images of the sequence of images used for extracting dynamic features of the imaged objects have normally a lower resolution. In any case the time dependent behaviour of the imaged objects acquired by the sequence of images can also be used in this case for establishing morphology features of the imaged objects.

In the segmentation step either carried out by the detection module or by the subsystem for extracting dynamic features in the images different image objects are detected and identified which corresponds to pixel clusters or groups which appearance is determined by a certain feature or quality of the corresponding region of the imaged body which feature or quality causes the said regions to interact in a specific way with the physical means for acquiring the image.

In the following step the detected and identified image objects are analysed relatively to their morphology, i.e. shape, dimension, symmetry, density, texture, tumour signs, etc.

This step which comprises a series of sub-steps which will be described with greater detail in the following description, allows to make a sorting of the image objects relatively to the fact if these image objects and the corresponding regions of the imaged body can be considered as having a certain searched feature or quality basing only on the extracted parameters describing the morphology of the image object and thus of the corresponding region of the imaged body and on the comparison of the said parameters with the parameters describing the typical morphology of regions of imaged bodies which have the said certain features or qualities.

Thus a certain number of false positives can be already sorted out from the image objects potentially corresponding to regions of the imaged body having the searched certain feature or quality only by means of these morphological criteria.

The images used as input data can be any kind of digital image data either two dimensional or three dimensional image data. Furthermore the image data used can be acquired in parallel by means of different imaging techniques. In the field of diagnostic imaging the images can be radiographic images, ultrasound images and MRI images. These images of the same body or of the same anatomical district of the same body can be all subjected to image processing according to the present method and the image data of the processed images according one or more steps of the previously described method of the present invention can all contribute as input data for the classification module.

Furthermore considering MRI images two kinds of useful MRI images can be acquired. These two kinds of images are the so called T1-weighted images and the T2-weighted images. This MRI image acquisition techniques are well known and differentiate themselves in a different response of the imaged body, particularly of the water and fat tissue present in the imaged body which leads to different appearance of the pixels in the images acquired corresponding to water and fat tissue.

According to a further feature of the method of the present invention, also the MRI T2 weighted images of the body under examination are acquired and the image data acquired can be directly used as additional input data of the classification module or as input data of one or more processing steps of the detection module and/or of the subsystem for extracting dynamic features, which output image data is than used as additional input data for the classification module.

In order to use the modified image data generated by processing T1 weighted MRI images and/or T2 weighted MRI images and/or eventually images of the same body acquired with other alternative imaging techniques by means of the detection module and/or by the subsystem for extracting dynamic features these modified image data has to be parameterized and transformed in a vector form which can be read and handled by the classification tools of the classification module.

According to a further feature of the present invention which is particularly relevant in the case the certain features searched are at least two, the classification module comprises at least two classification steps each one is specifically trained and directed to the assessment of the existence of one of the at least two features or qualities.

This has a great relevance and practical meaning. Consider for example the problem of identifying tumour tissue in an anatomical district. Since tumour tissue can be of two kinds, namely benign and malignant, a first classification step is only directed in determining the presence of lesions in the imaged body, while the second classification step is only directed in determining which lesion is to be considered benign and which lesions has to be considered malignant.

A particular embodiment of the method of present invention considers making use of each classification step of different classification tool or algorithm each one specifically trained for determining respectively the first feature and the second feature.

So in the case that the searched first feature consists in tumour tissue and the second feature in the benign or malign quality of this tissue, a first classification tool or algorithm is trained for evaluating the image relatively to the existence of generic tumour tissues and the second classification tool or algorithm is trained specifically for evaluating it the identified tumour tissues by the first classification tool or algorithm are benign or malign.

Output data of the classification module can be visualized either in alphanumeric data or also with a modified image where the pixels of the processed image being considered corresponding to an object of the imaged body having the searched feature are highlighted by giving to them a particular aspect such as a particular colour or brightness.

When more than a feature or quality is searched, for example when benign and malign tumour tissues are searched than the pixels corresponding to objects or regions of the imaged body which has been classified as having the said features are further provided with a different appearance.

According to a further feature of the present method, the highlighting of individual or multiple pixels of the image which as a result of the classification process has been determined as corresponding to an imaged object having a certain feature or quality is carried out by giving to the said number of pixels a certain predefined output visual characteristics such as colour.

So for example when considering the special problem of determining whether the imaged objects identified in an imaged body are benign or malignant tumour lesions, pixels of the image corresponding to objects considered as being benign tumour lesions may be coloured in blue or green colour while pixels corresponding to objects considered as being malign tumour lesions may be coloured in red colour.

These colours are predefined and are applied to the pixels of the object depending on the output data of the classification module.

When using Artificial Neural Networks for determining the presence of a feature or quality in an image generally the output layer of the Artificial Neural Network is provided with one or more output knots and the absence or the existence of the searched feature is defined by a numeric value a knot can assume.

According to an improvement of the method of the present invention it is possible to use the values of the output knots for generating an highlighted appearance of the pixels of the processed image which also considers the fuzzy output of the Artificial Neural Network.

According to the above mentioned improvement of the method of the present invention, for the purpose of displaying the output information of a classification algorithm each output node is uniquely assigned to an image parameter defining the colour space according to one colour models such as RGB, or the HSV or the HIS models. In this case the value of each output knot can be uniquely associated to a value of the chosen colour model such as one RGB value or the HUE value or other combinations of these values depending on the number of output knots provided in the output layer of the Artificial Neural Network.

This method step can be applied also if the Artificial Neural Network has two or more knots or using Artificial Neural Networks in a cascade.

In this last case, it is possible to use the output of each of these to code part of the values or all the values of the colour model which has been chosen. As an example when considering for instance a RGB colour model the R parameter could be determined by the output of a first Artificial Neural Network in the cascade of Artificial Neural Network, the G parameter could be determined by the output of a second Artificial Neural Network in the cascade of Artificial Neural Network. The B parameter of the RGB colour model could be determined by a fixed value if only two Artificial Neural Networks are present or by a combination of the outputs of the two Artificial Neural Networks. When a third Artificial Neural Network is provided in the cascade of Artificial Neural Networks, than the B parameter could be determined by the output value of this third Artificial Neural Network or by a combination of the output of this third Artificial Neural Network with the outputs of one or both the first and the second Artificial Neural Network.

Thus using the above described method it is possible to visualize the fuzzy output of the classification module with a more detailed way relating to the classification results giving to the person who reads the output image a more precise feeling or way to visually evaluate the results furnished as an output by the classification module.

Since there are well defined mathematical relations between each colour models any colour model of the colour space can be used.

Although the above example is made with reference to Artificial Neural Networks as classification tools or algorithm, it is obvious for the skilled person that the same method could be applied also to other kind of classification tools or algorithms, since in any case the results of these classification tools or algorithms relating to the assessment of a certain feature or quality requires a parameterisation of the said results and thus consist in numerical values which indicates presence, absence of the searched feature or quality or an intermediate condition which is a condition of indefiniteness of the classification result relating to the problem of assessing presence or absence of the searched feature or quality.

Particularly relatively to the steps <of visualizing the fuzzy output it has to be stressed out that not only Artificial neural networks has fuzzy output, but also other families of classification algorithms and that this fuzzy output values can be represented by providing a correlation rule between the output of the classification algorithm and RGB model or other image models.

It has to be stressed out that the single steps of image processing of either the detection module, the subsystem for extracting dynamic features and the classification module are in principle known image processing steps which are used as single and separate tools partly in image processing of diagnostic images partly in other fields where image processing is carried out such as in arts or in industrial processes.

So relating to the processing steps and tools provided in the detection module and in the classification module the following list of publication and documents describes these steps and tools in greater detail:

A more detailed description of digital image processing is made in:

Image segmentation is discussed with greater detail in:

1. Middleton I, Damper R I. Segmentation of magnetic resonance images using a combination of neural networks and active contour models. Med Eng Phys 2004; 26:71-86
2. Grau V, Mewes A U, Alcaniz M, Kikinis R, Warfield S K. Improved watershed transform for medical image segmentation using prior information. IEEE Trans Med Imaging 2004; 23:447-458
3. Lucier B J, Kallergi M, Qian W, DeVore R A, Clark R A, Saff E B, Clarke L P. Wavelet compression and segmentation of digital mammograms. J Digit Imaging 1994; 7:27-38

Image registration is described with more detail in:

1. Sorzano C O, Thevenaz P, Unser M. Elastic registration of biological images using vector-spline regularization. IEEE Trans Biomed Eng 2005; 52:652-663
2. Crum W R, Hartkens T, Hill D L. Non-rigid image registration: theory and practice. Br J Radiol 2004; 77 Spec No 2:S140-53
3. Park H, Bland P H, Brock K K, Meyer C R. Adaptive registration using local information measures. Med Image Anal 2004; 8:465-473
4. Kim J, Fessler J A. Intensity-based image registration using robust correlation coefficients. IEEE Trans Med Imaging 2004; 23:1430-1444
5. Pluim J P, Fitzpatrick J M. Image registration. IEEE Trans Med Imaging 2003; 22:1341-1343

Contrast Agent uptake curves and methods for determining the said curves are described in:

1. Daldrup-Link H E, Brasch R C. Macromolecular contrast agents for MR mammography: current status. Eur Radiol 2003; 13:354-365
2. Sardanelli F, Iozzelli A, Fausto A. Contrast agents and temporal resolution in breast MR imaging. J Exp Clin Cancer Res 2002; 21:69-75
3. Baum F, Fischer U, Vosshenrich R, Grabbe E. Classification of hypervascularized lesions in CE MR imaging of the breast. Eur Radiol 2002; 12:1087-1092
4. Turetschek K, Roberts T P, Floyd E, Preda A, Novikov V, Shames D M, Carter W O, Brasch R C. Tumor microvascular characterization using ultrasmall superparamagnetic iron oxide particles (USPIO) in an experimental breast cancer model. J Magn Reson Imaging 2001; 13:882-8
5. Ercolani P, Valeri G, Amici F. Dynamic MRI of the breast. Eur J Radiol 1998; 27 Suppl 2:S265-71
6. Tofts P S. Modeling tracer kinetics in dynamic Gd-DTPA MR imaging. J Magn Reson Imaging JID-9105850 RN-0

(Contrast Media) RN-0 (Organometallic Compounds) RN-0 (Radioactive Tracers) RN-67-43-6 (Pentetic Acid) RN-80529-93-7 (Gadolinium DTPA) 1997; 7:91-101
7. Griebel J, Mayr N A, de Vries A, Knopp M V, Gneiting T, Kremser C, Essig M, Hawighorst H, P. H. L, Yuh W. Assessment of tumor microcirculation: a new role of dynamic contrast MR imaging. J Magn Reson Imaging JID-9105850 RN-0 (Antineoplastic Agents) RN-0 (Contrast Media) RN-0 (Radioactive Tracers) RN 7440-54-2 (Gadolinium) 1997; 7:111-9
8. Hoffmann U, Brix G, Knopp M V, Hess T, Lorenz W J. Pharmacokinetic mapping of the breast: a new method for dynamic MR mammography. Magn Reson Med 1995; 33:506-14

The use of classification algorithms and particularly the use of Artificial Neural Networks as well as the way of coding pixels or voxels for the processing of an image by means of a classification algorithm are disclosed in:
1. Szabo B K, Wiberg M K, Bone B, Aspelin P. Application of artificial neural networks to the analysis of dynamic MR imaging features of the breast. Eur Radiol 2004; 14:1217-1225
2. Szabo B K, Aspelin P, Wiberg M K. Neural network approach to the segmentation and classification of dynamic magnetic resonance images of the breast: comparison with empiric and quantitative kinetic parameters. Acad Radiol 2004; 11:1344-1354
3. Vomweg T W, Buscema M, Kauczor H U, Teifke A, Intraligi M, Terzi S, Heussel C P, Achenbach T, Rieker O, Mayer D, Thelen M. Improved artificial neural networks in prediction of malignancy of lesions in contrast-enhanced MR-mammography. Med Phys 2003; 30:2350-2359
4. Perez de AlR, Ruiz-Cabello J, Cortijo M, Rodriguez I, Echave I, Regadera J, Arrazola J, Aviles P, Barreiro P, Gargallo D, Grana M. Computer-assisted enhanced volumetric segmentation magnetic resonance imaging data using a mixture of artificial neural networks. Magn Reson Imaging 2003; 21:901-912
5. Lucht R E, Knopp M V, Brix G. Classification of signal-time curves from dynamic MR mammography by neural networks. Magn Reson Imaging 2001; 19:51-7
6. Markopoulos C, Kouskos E, Koufopoulos K, Kyriakou V, Gogas J. Use of artificial neural networks (computer analysis) in the diagnosis of microcalcifications on mammography. Eur J Radiol 2001; 39:60-5
7. Vergnaghi D, Monti A, Setti E, Musumeci R. A use of a neural network to evaluate contrast enhancement curves in breast magnetic resonance images. J Digit Imaging 2001; 14:58-59
8. Abdolmaleki P, Buadu L D, Naderimansh H. Feature extraction and classification of breast cancer on dynamic magnetic resonance imaging using artificial neural network. Cancer Lett 2001; 171:183-91
9. Chen D R, Chang R F, Huang Y L, Chou Y H, Tiu C M, Tsai P P. Texture analysis of breast tumors on sonograms. Semin Ultrasound CT MR 2000; 21:308-316 and more generally in:
1. Buscema M. A brief overview and introduction to artificial neural networks. Subst Use Misuse 2002; 37:1093-1148
2. Haykin S. Neural Networks: A Comprehensive Foundation, 2 ed. New York: Macmillan, 1999
3. Buscema M. Artificial neural networks and complex social systems. I. Theory. Subst Use Misuse JID-9602153 1998; 33:v-xvii, 1-220 FAU-Bu
4. Buscema M. Theory: Foundation of Artificial Neural Networks. Substance Use & Misuse 1998; 33:28-98.

Relating to the basic concepts of the colour spaces and the models describing them a disclosure is made in the on-line encyclopaedia called Wikipedia at the pages http://en.wikipedia.org/wiki/Color_theory and http://en.wikipedia.org/wiki/Color_space and corresponding links.

Available on the market there are different image processing systems such as CAD-stream® and CADalyst® by Confirma Inc. which are a pure detection tools.

Further improvement of the method according to the present invention are subject matter of the dependent claims.

Relating to the method of the present invention it is to be noticed that as a general teaching instead of carrying out the classification process pixel by pixel or voxel by voxels as known in the state of the art, the classification is carried out at the level of the objects identified in the image by means of the detection tool and the variables univocally coding each object are formed at least by the parameters describing the morphology of such objects and or also by the dynamic features extracted by the subsystem for extracting dynamic features as well as eventually by other parameters describing features of the objects in other images acquired with other imaging techniques or with variants of an imaging technique. It is important to to stress out that this kind of coding of the information contained in the image is closer to the real problem which has to be solved by means of the computer aided diagnostic process. Indeed diagnostic images are acquired for determining whether a pathologic object is present in the imaged region and not if some pixel or voxel relates to certain features or qualities of the imaged region particularly of the imaged tissues. The processing of the image basing on the objects individuated therein helps in reducing the computational burden by limiting the number of different records to be processed by the classification module.

The invention relates also to a system and to a software for processing and evaluating images, particularly diagnostic images.

Further details and the corresponding advantages of the method according to the present invention will be disclosed in the following description by means of an example and of the annexed drawings in which:

FIG. 14 is a table listing the different parameters that can be obtained by the step according to the example of FIG. 13.

FIG. 20 is an example of the graphic and alphanumeric output of the entire image processing and evaluation method according to the present invention.

Figure 1:
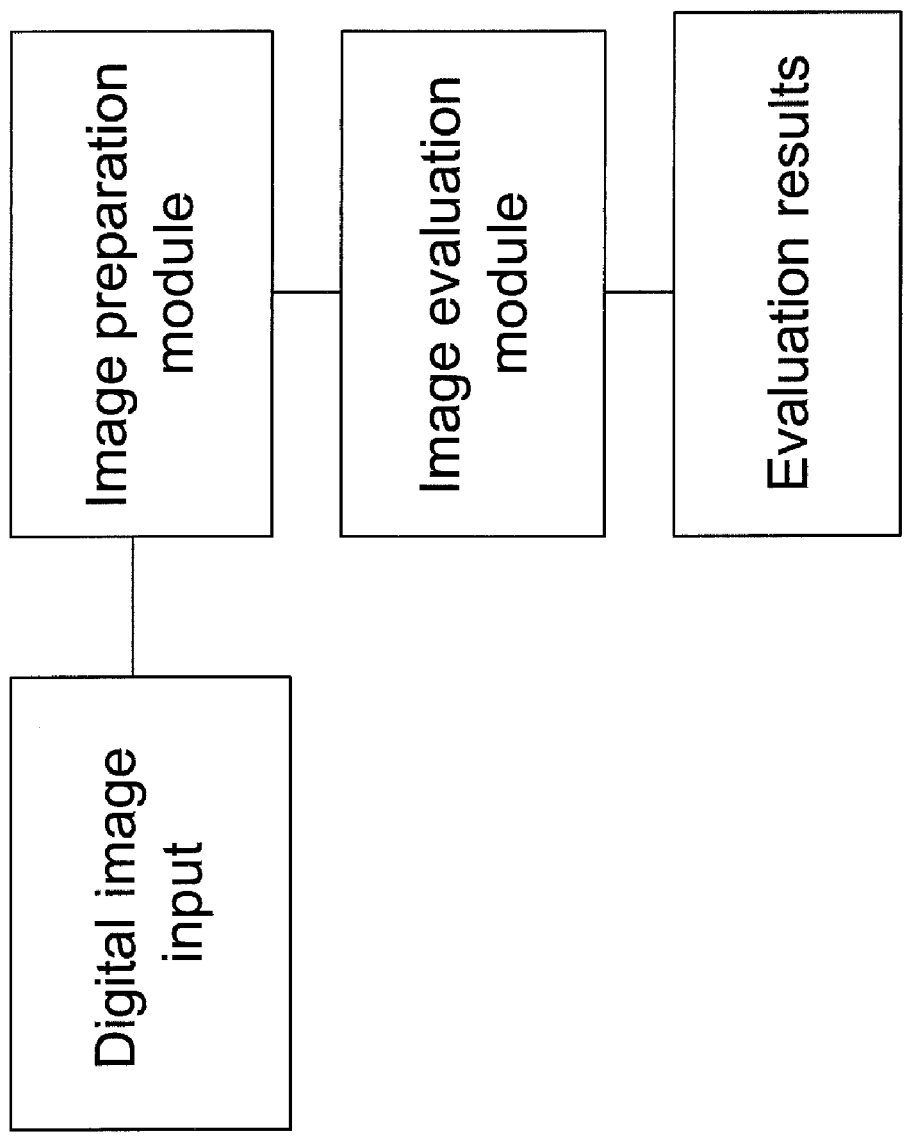
FIG. 1 is a schematic block diagram illustrating the structure of a system for image processing and evaluation applying the method according to the present invention

Generally speaking an image is a projection of the physical real world in a virtual world. Two dimensional images can be projections of a three dimensional real scene in a two dimensional space or so called slices which are not projections but the image of the physical world along a certain section plane intersecting the three dimensional physical world. Images are acquired by means of physical interaction of the physical world with physical means typically any kind of beams or radiation. The X-rays or magnetic pulses emitted by the physical world is generally not spontaneous but is the result of an interaction with radiation or beams being naturally provided in the physical world such as light or being specifically generated for acquiring the image due to special interaction mechanisms of the chosen kinds of beams or radiation and the physical world to be imaged.

The physical world can be considered as being formed by objects which will have a corresponding image object on the image of the physical world. The topology of the physical world is reproduced in the image as far as the physical means for acquiring the image are able to interact with the physical world. So spatial relation of the objects and their shape and other features are reproduced in the virtual representation of the real physical world of the image.

Image processing is used to various extents as correcting images which due to various effects are affected by acquisition errors or also to recognize the presence of various image objects which are the representation of objects in the real physical world. Generally this image processing is aimed at recognizing the presence of certain target objects of the real physical world which has been imaged and are present in the image as image objects. These target objects differentiate themselves from other objects in the real world and in the image from other objects which are not of interest.

Several criteria and corresponding image processing methods can be applied depending on the features of the searched target objects. The features of the target objects determine the way of interaction of the said target objects with the means for acquiring the image and for which the corresponding image objects have a specific visual appearance.

Particularly in diagnostic imaging, criteria for determining the nature, kind or other features or qualities of the imaged objects by means of their appearance in the image consist in the evaluation of the intensity of the signal generated by the means for acquiring an image and which has a correspondence in the appearance of the pixel or voxel in the image, generally a grey-scale image, the relation of the appearance of each pixel and voxel with the appearance of other pixel of the surroundings, the shape and other morphology parameters of the image object and further to this also the behaviour in time of the imaged objects which can be spontaneous or induced by generating certain conditions causing a time dependent behaviour of the imaged objects.

Diagnostic images are generally grey-scale images in which the appearance of each pixel is univocally related to the parameters defining the signals which are generated by the physical means for acquiring the image.

According to FIG. 1 the method for processing and evaluating digital images, particularly diagnostic images comprises two principal modules an image preparation module also called detection module indicated with 1 and an image evaluation module also called classification module indicated with 2. Digital images are furnished to the input 3 of the detection module 1 which carries out a series of image processing steps according to different image processing tools. The output of the detection module provides for processed or modified image data which are used to generate the input data of the classification module 2. Herein the single pixels of the images are analysed relatively to the fact if they represent a dot, a region or a part of the imaged body which has certain searched features or qualities. Classification data are outputted at 4 in an alphanumerical format or as a modified image in which the pixels corresponding to the said dots, regions or parts of the imaged body which have a certain searched features or qualities are highlighted relatively to all the other pixels of the image.

Images can be acquired by any kind of imaging technique and particularly by means of radiographic, ultrasound or nuclear magnetic imaging techniques according to one or more of the known variants which are typical for these techniques. The method according to the invention is explained and disclosed by means of its application to the processing of diagnostic images and particularly of diagnostic images directed to the detection of tumour tissues either benign or malignant. The specific example by means of which the method is disclosed regards MRI images of the breasts for the diagnosis of breast cancer. Nevertheless it is clear and the following description will help in understanding that the method according to the present invention can be applied for the diagnosis of other kind of lesions or pathologies in other anatomical districts. Furthermore the method of the present invention can be also applied to fields which are very different form the medical diagnostic.

Figure 2:
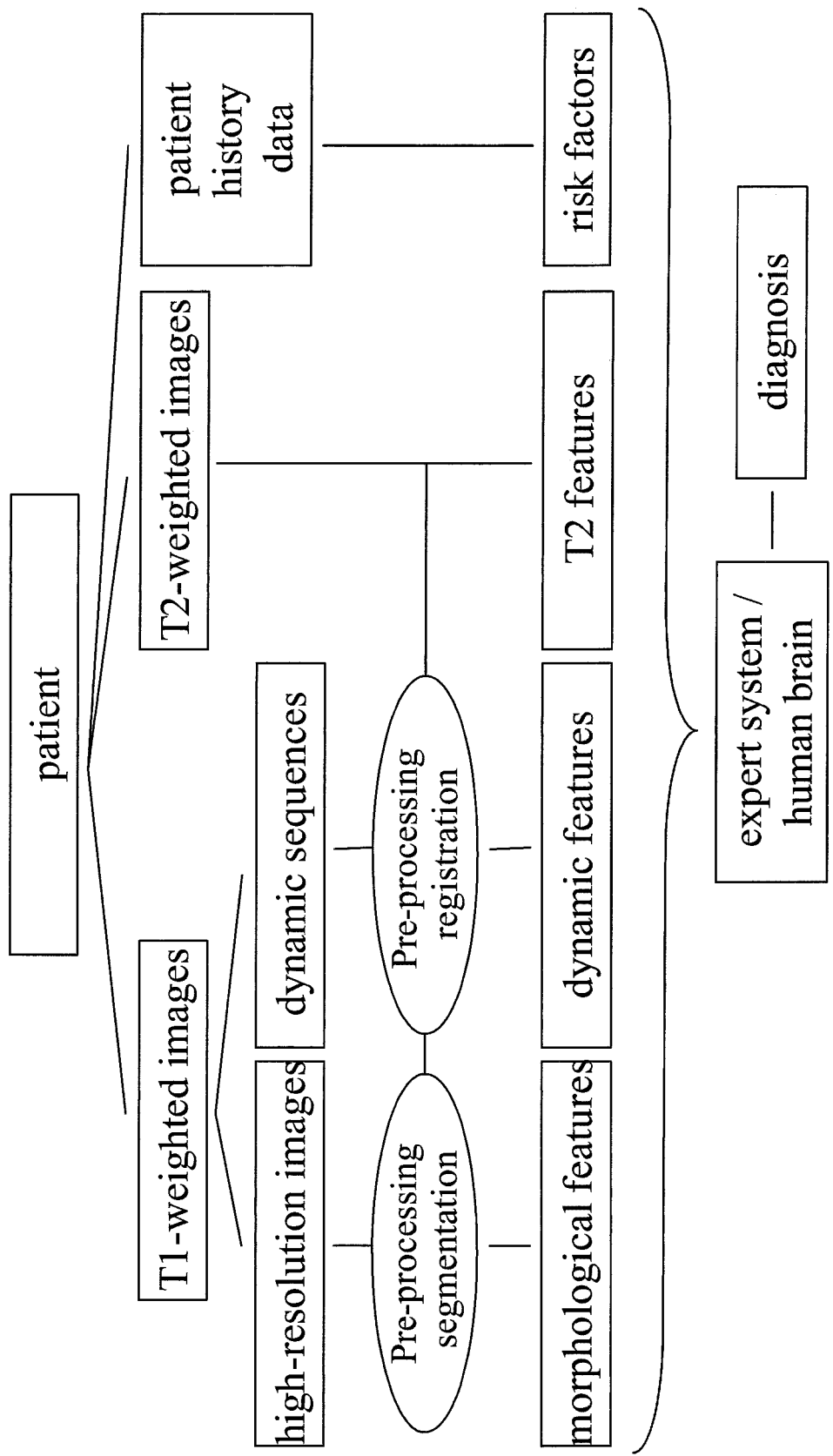
FIG. 2 illustrates a more detailed schematic block diagram of an embodiment of a system applying the method present invention.

An example of a workflow of the method of the present invention is represented in the diagram of FIG. 2.

Images, particularly MRI images of an anatomical district of a patient (in this case of the breast) are acquired. As disclosed in FIG. 1 this images are subjected to processing in a first detection module. As it will appear more clearly in the following description, the detection module is based on image processing directed to the detection of pixels of a two dimensional image or voxels of a three dimensional image of an anatomical district of the patient (in this case of the breasts) which appearance is determined by the way of interaction of the corresponding dot or region of the imaged body with the physical means for acquiring the image and which way of interaction corresponds to the way of interaction which is typical for the tissues having the searched features or qualities, namely tumour lesions either benign and malignant. As it will be appear more clearly from the following description further criteria can be considered such as intensity level of the pixels, or morphology parameters of a group of pixels related to the same object (such as a lesion or a suspected lesion) in the imaged body.

The result of the detection processing step is a modified image in which the pixels of the image representing the areas of the imaged body having the searched features or qualities (such as a tumour region) are highlighted with respect to the other pixels of the image. Thus modified image consist in modified imaged data.

Considering the example of FIG. 2 where MRI technique is used for acquiring two dimensional or three dimensional images of the body under examination two kinds of images can be acquired which are defined as T1-weighted images and T2-weighted images. This two kinds of acquiring the image are well known to the skilled person and the resulting images are differentiated by the different appearance of the pixels of the image corresponding to fat tissue or water in the imaged body.

T1-weighted images and/or also T2-weighted images can be used either for detecting static images from which morphological information of the imaged body can be extracted or for extracting so called dynamic features of the imaged body or regions of it. Such dynamic features consist for example in the well known perfusion parameters or signal intensity/time-curves which are obtained when acquiring a sequence of images of the same body or region thereof in which a so called contrast media is present. Also perfusion behaviour of certain zones or objects in the imaged body is a typical criteria for detecting a quality or feature of the imaged body or zones thereof. When searching tumour lesions, the signal intensity/time-curve behaviour is very important since this kind of lesions are characterised by an increased vascularisation and thus show a very specific signal intensity/time-curve which can be used for detecting the features or qualities of the imaged body or of regions thereof particularly in the present example the tumour lesions.

Typically T1 weighted images used for extracting morphological features of regions or objects in the imaged body represented in the image are high resolution images, while the images for extracting dynamic features based on a time dependent behaviour of the said regions or objects in the imaged body such as their dynamic behaviour have generally a lower resolution.

In the present example T2 weighted images are used only for detecting features relating to fat tissue or water.

As it appears from FIG. 2 in parallel to the detection module a subsystem is provided for processing the sequences of images acquired for extracting time dependent behaviour of the imaged tissues, i.e. the regions or objects in the imaged body.

The detection module comprises a so called segmentation step which is commonly used either for the static images and for the sequence of images. Thanks to these morphological features of the imaged region or objects which are present in the imaged body can be defined by means of the static images and also of the sequence of images acquired for determining the time dependent behaviour.

The subsystem for extracting dynamic features from the sequence of the images is provided with a so called registration tool which operates for eliminating artefacts from the images due to movements of the patient. Many kinds of registration tools are known as it is indicated by the above cited published references The registered images of the sequence of images are then compared, particularly subtracted one from the other in order to determine changing signal intensities of pixels/voxels in time. Particularly when a dynamic signal intensity/time-curve measurement is carried out, than each image of the sequence of images which are acquired after that a contrast media is provided in the imaged body is subtracted from an image of the body acquired at a time when no contrast media was present in the imaged body.

As it will be discussed with greater detail in the following the dynamic features can be obtained by the signal intensity/time-curves which describe the variation in time of the said image differences for each image of the sequence of images.

The registered images can be also subjected to a segmentation step which is used to detect in the images different objects which are represented in the images by pixels having certain intensity levels as sorted out by means of a discrete level scale.

The image areas which are obtained by the segmentation process are defined as image objects and are further subjected to the processing by means of a tool for extracting morphological features of the said objects.

The morphological features determined by the detection module, the dynamic features determined by the subsystem for extracting the dynamic features, eventually the image data of the T2 weighted image are used to code each object of the image or of the images with a vector which is fed to an expert processing tool for evaluating the image. This expert processing tool is typically a classification tool such as a predictive algorithm or a chain or combination of predictive algorithms connected in a cascade. This tools are part of the classification module defined in the previous description and can be trained by implementing knowledge or empirical experience so that the tool is able to collect experience and evaluate the images basing of this experience. Typical classification tools are so called Artificial Neural Networks of which ever kind, clustering algorithm, or other statistical predictive or classification algorithms which are part of the technical knowledge of the skilled person.

As it appears from FIG. 2 further information can be added to the vector coding each pixel of the image for carrying out the classification or the evaluation step. In this case patient history and/or anagraphical data are considered which are processed in such a way as to determine risk factors which are added to the information of the vector for coding each pixel of the image.

Figure 3:
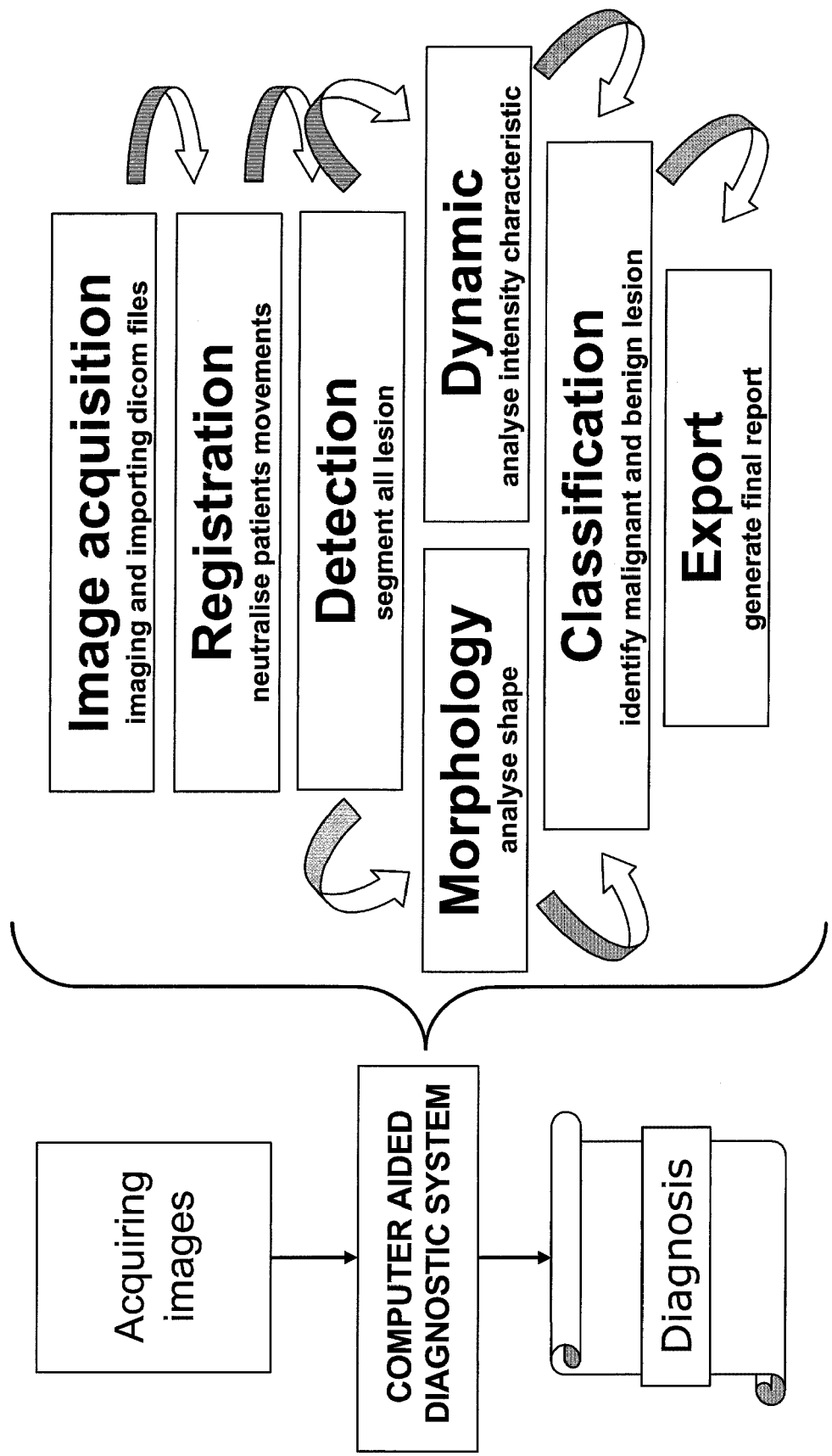
FIG. 3 is a block diagram illustrating the relation of the steps of the entire chain of diagnostic imaging and processing and evaluation.

In the diagram of FIG. 3 the imaging and the image processing chains are illustrated according to an example of the method of the present invention.

The principal chain comprises the steps of acquiring the image or several images. The image data are then submitted to a computer aided diagnostic system which processes the image data and carries out an automatic evaluation of the images relating to prescribed criteria for individuating certain indications of features, qualities or pathologies in the region of the body of which the image are acquired and by means of the information provided by this images. These indication has to be furnished either in an alphanumeric for or in a graphic form or with a combination of these forms to the medical staff which basing on the indication of the computer aided diagnostic system generate a diagnosis.

Computer aided diagnostic system according to the present invention is based on software means which carry out following steps of the method according to the present invention of which FIG. 3 illustrates an example in the diagram at the right part of FIG. 3.

Figure 4:
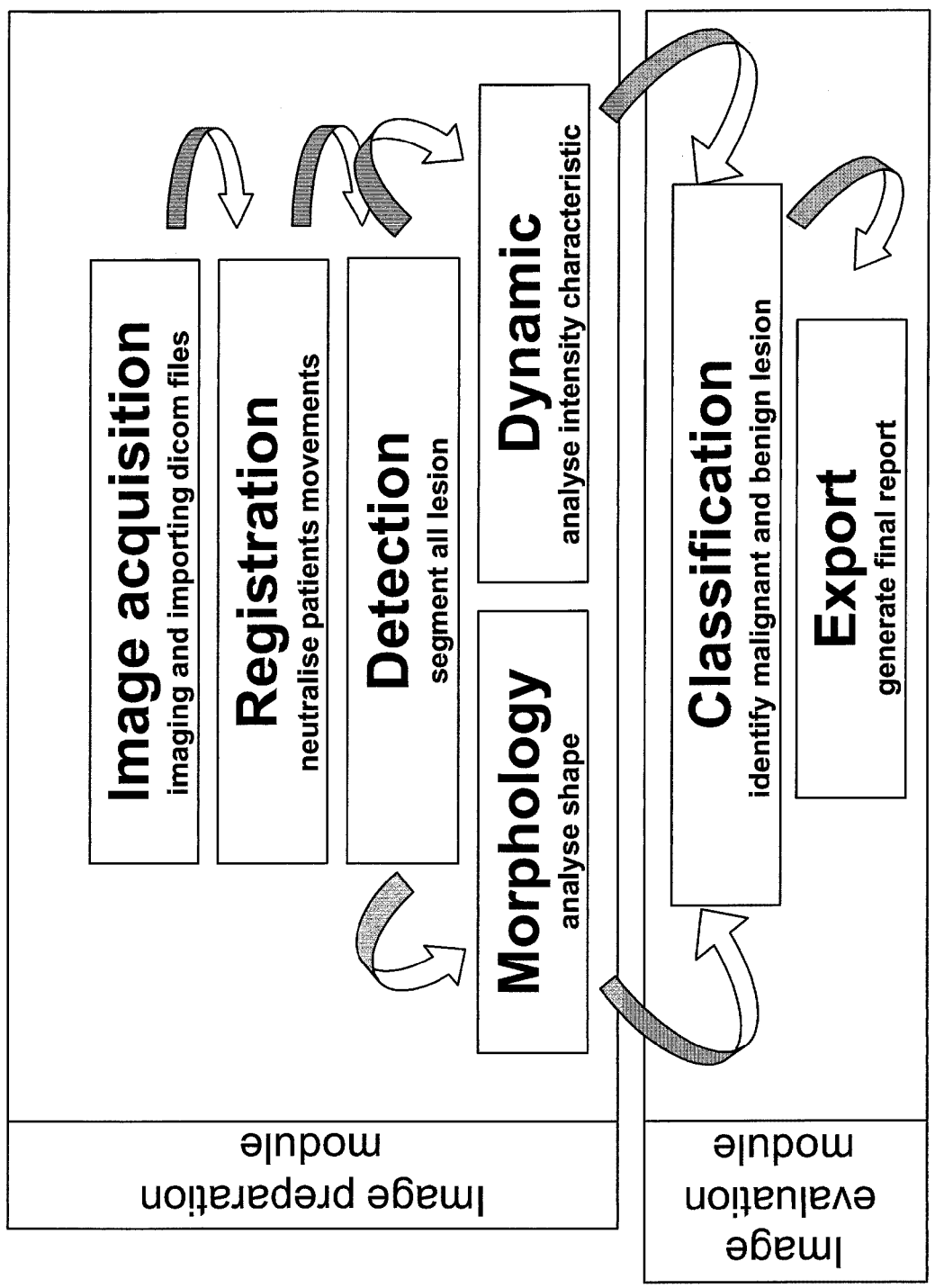
FIG. 4 is a block diagram showing the steps of each image processing module provided in an example of the method according to the present invention.

Relating to this example it has to be noticed that the detection module or image preparation module as better indicate by FIG. 4, the processing of T2 weighted images and the processing of high resolution T1 weighted static images is not considered but the sample is limited to the treatment of a sequence of images which, as described in relation of the more complex examples of FIG. 2, can also be used either for preparing the images relating to the detection of morphological features of the imaged objects and for the determination of the dynamic features of the imaged objects. This is the more complex case, since as it appears clearly from the previous description of the example of FIG. 2, the subsystem for extracting dynamic features further to making use of a sequence of images also needs a preprocessing step of registration of the images of the sequence before carrying out a segmentation step which is a typical step of the detection module. So the image input data to the detection module are in this case the registered images of the sequence of images and not the high resolution images. The way in which the detection module processes the said images is completely independent from the images and thus the example of FIGS. 3 and 4 applies mutatis mutandis to high resolution static images with the omission of the registration step which is not necessary in this case.

In the first step the image data of the acquired images are converted in file format typically the well known DICOM file format and are subjected to a registration processing step. This is a well known step which is important for eliminating images artefacts which are due to patient movements either voluntary or involuntary such as due to physiological effects such as movements induced by the heart beats and/or by breathing. Many techniques for carrying out registration are known. Particular techniques are disclosed with greater detail in the following publications:

1. Sorzano C O, Thevenaz P, Unser M. Elastic registration of biological images using vector-spline regularization. IEEE Trans Biomed Eng 2005; 52:652-663
2. Sivaramakrishna R. 3D breast image registration—a review. Technol Cancer Res Treat 2005; 4:39-48
3. Crum W R, Hartkens T, Hill D L. Non-rigid image registration: theory and practice. Br J Radiol 2004; 77 Spec No 2:S140-53
4. Pluim J P, Maintz J B, Viergever M A. F-information measures in medical image registration. IEEE Trans Med Imaging 2004; 23:1508-1516
5. Cao Z, Pan S, Li R, Balachandran R, Fitzpatrick J M, Chapman W C, Dawant B M. Registration of medical images using an interpolated closest point transform: method and validation. Med Image Anal 2004; 8:421-427
6. Kim J, Fessler J A. Intensity-based image registration using robust correlation coefficients. IEEE Trans Med Imaging 2004; 23:1430-1444
7. Chandrashekara R, Mohiaddin R H, Rueckert D. Analysis of 3-D myocardial motion in tagged MR images using nonrigid image registration. IEEE Trans Med Imaging 2004; 23:1245-1250
8. Pluim J P, Fitzpatrick J M. Image registration. IEEE Trans Med Imaging 2003; 22:1341-1343

Figure 5:
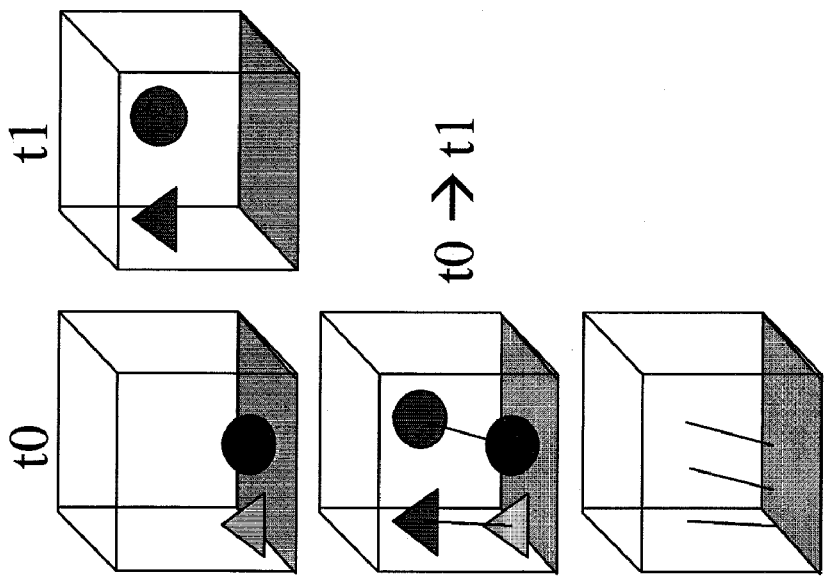
FIG. 5 is a schematic representation of the principal steps of the image registration.

FIG. 5 illustrates the general steps carried out by known registration processes. Two images, particularly here two three dimensional images which has been acquired at different times t0 and t1 are illustrated by means of the two cubes at the right side of the figure. As a first step of the registration process the first image is analysed for determining a certain number of relevant objects in the form of single pixels or voxels or in the form of groups of pixels or voxels defining certain objects in the image which can be easily identified with respect to the other pixels or voxels or to other objects in the image. These pixels or voxels or groups of pixels or voxels or objects are defined as landmarks and are analysed relating to their reliability as landmarks.

Once a certain number of reliable landmarks has been determined the said landmarks are subjected to a tracking step. This step consist in finding out the same landmarks in the second image acquired a the time t1. In the right hand examples of FIG. 5 the landmarks are schematically represented as a triangle and a circle. Once the said landmarks has been individuated in the second image displacements vectors are defined. These displacement vectors which can show different orientation and modulus for different landmarks since biologic tissues are non rigid structures are used to generate global and local vector fields which defines global and local movement vector fields spread over the image plane. Applying global and local movement vector fields to the second image is a so called morphing step which eliminates the patient movements effect on the imaged region and the corresponding artefacts. The tracking step and the morphing vector field are illustrated at the right side of FIG. 3 with the cube representing the three dimensional image and the arrows between the geometrical objects representing the landmarks. In the last cube the movement vector field is illustrated by means of the arrows. The local movement vectors of the two landmarks (triangle and circle) and the vector field have non equal direction of the vectors as it appears from the said graphical representations in FIG. 5. Image registration has to be carried out for each image of sequence of images.

Registered images can be thus submitted to two different kinds of processing by processing the registered images with the detection module and the subsystem for extracting dynamic features. In both cases the registered images can be processed with a so called segmentation tool. Segmentation processing analyses pixel or voxel features of the registered images in order to determine groups of pixels which based on intensity criteria of the pixel in the image may be considered as being part of a common kind of object. Through this segmentation step a certain number of objects can be individuated in the images and this objects can be handled as a unitary element for the purposes of other processing steps.

Also segmentation is a known technique. More detailed information about segmentation is disclosed in:

1. Middleton I, Damper R I. Segmentation of magnetic resonance images using a combination of neural networks and active contour models. Med Eng Phys 2004; 26:71-86
2. Grau V, Mewes A U, Alcaniz M, Kikinis R, Warfield S K. Improved watershed transform for medical image segmentation using prior information. IEEE Trans Med Imaging 2004; 23:447-458
3. Sha D D, Sutton J P. Towards automated enhancement, segmentation and classification of digital bran images using networks of networks. Information Sciences 2001; 138:45-77
4. Ghanei A, Soltanian-Zadeh H, Windham J P. A 3D deformable surface model for segmentation of objects from volumetric data in medical images. Comput Biol Med 1998; 28:239-53

Some basic information about the segmentation processing steps are described in the following with the help of the FIGS. 6 and 7A to 7F.

Segmentation provides for subdividing the images in regions with similar properties thus detecting series of connected voxels which might also give information about the relation between the said regions. After having carried out the division of the images in this regions the said regions are defined as objects in the image.

As said before segmentation processing is carried out by individuating pixels or voxels or regions of the image comprising several pixels or voxels which have certain similar signal intensity features. Normally, this is carried out by defining intensity thresholds and applying these thresholds to intensity histograms of the images. According to the present method instead of using a fixed threshold an adaptive threshold is used.

Figure 6:
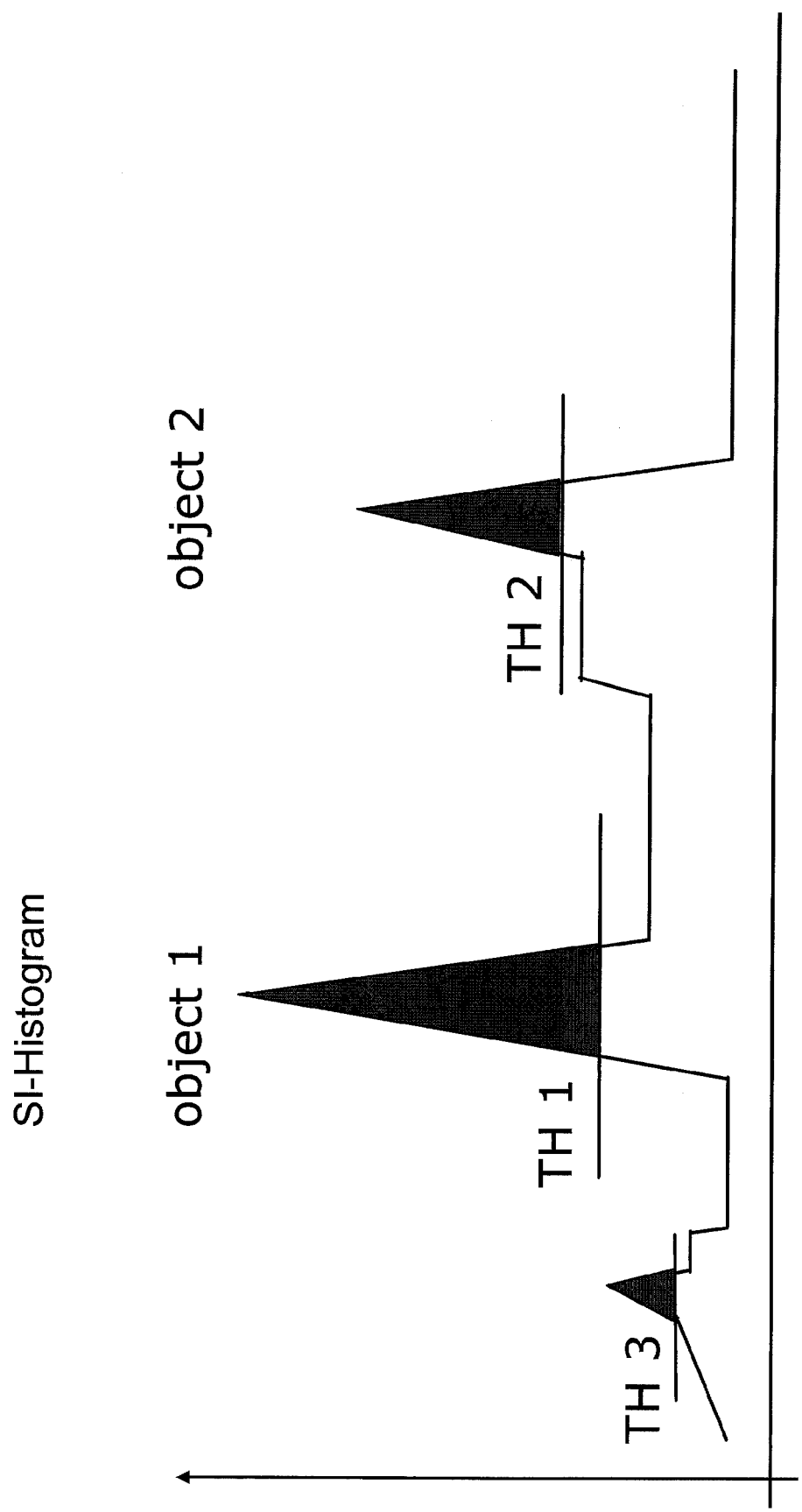
FIG. 6 illustrates a diagram of the principle for setting the thresholds used carrying out image segmentation.

FIG. 6 illustrates a simplified intensity histogram of an image. In this case the histogram is a two dimensional one but when considering images the intensity histogram is a surface.

The pixel intensity is represented in relation to the position of the pixels in the image and the adaptive threshold is represented by three different threshold values indicated with TH1, TH2 and TH3.

Each group of pixels or image region whose intensity lyes over the threshold are then defined as objects in the image.

The segmentation processing step making use of the adaptive threshold is carried out in an iterative way as it will be explained in the following by means of the FIG. 7A to 7F which are referred also to the example of FIG. 6.

Identification of object 1 which is related to the first threshold TH1 is carried out by identifying the maximum intensity as a second step the image is seeded with individuals thresholds determined by means of the said maximum intensity.

In order to find out a second class of objects indicated as object 2 the segmentation process provides the repetition of the above steps. This time the second highest intensity in the image is determined and a second individual threshold is determined. The image is the seeded with this second individual threshold TH2 and an image region is individuated corresponding the second object 2 is identified.

Next iterative step provides for individuating in the image a third highest intensity, determining a third individual threshold TH3 and seeding the image with this individual threshold in order to identify further objects. The segmentation iterative process is stopped when as occurring in this example with the third threshold the seeding of the image with the corresponding individual threshold does not lead to delimited regions of the image. At these steps segmentation process is stopped and the image is considered as showing only two objects.

Figure 7A:
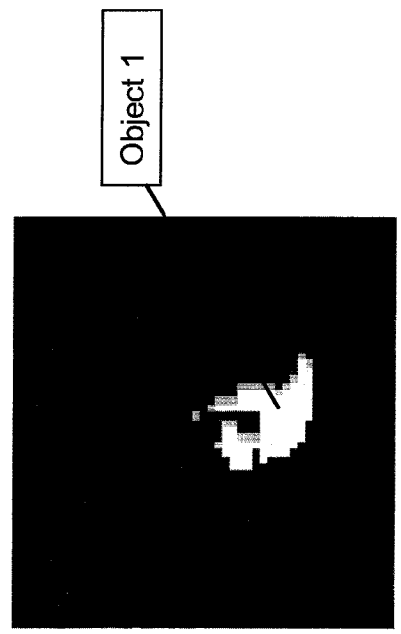
FIGS. 7A to 7F illustrates the steps of the image segmentation process applied to a typical image.
Figure 7B:
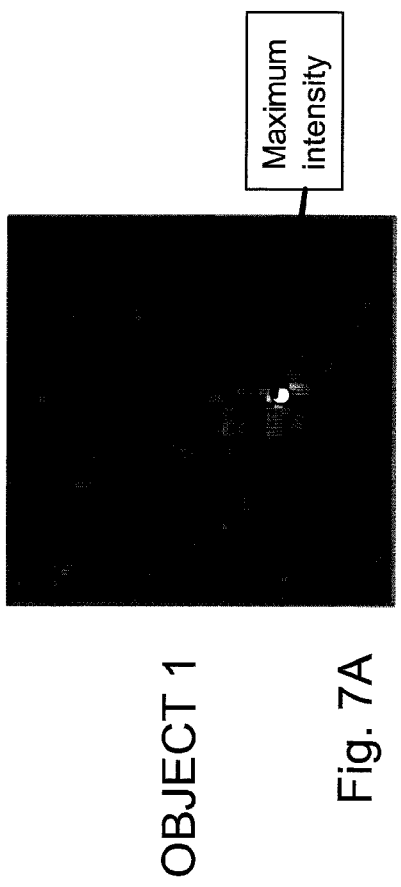
Figure 7C:
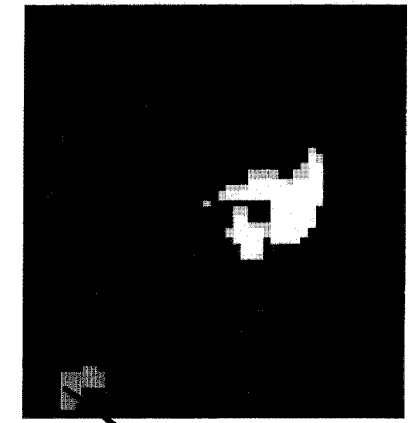
Figure 7D:
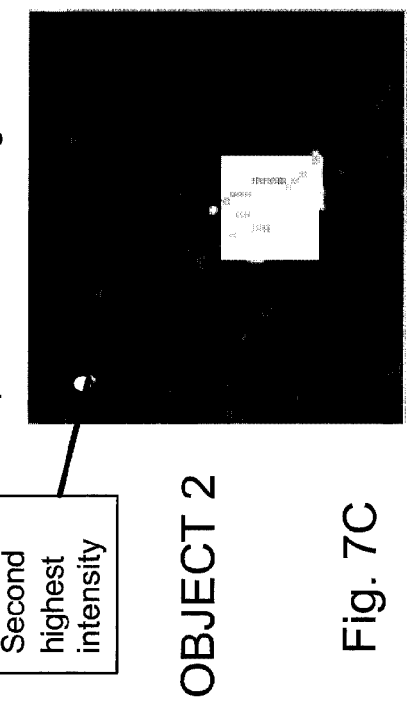
Figure 7G:
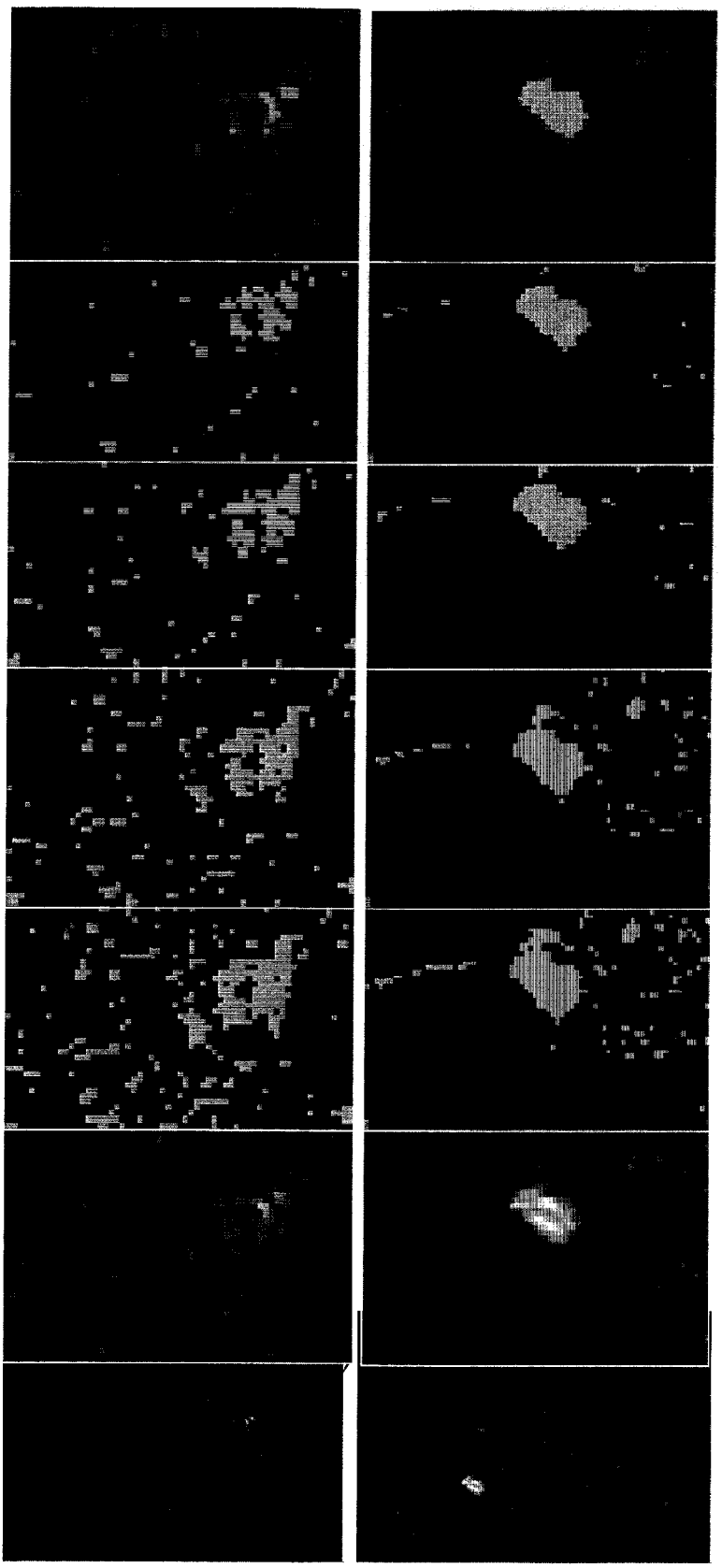

FIG. 7G illustrates the effect of segmentation on an enlarged particular of two different images using different thresholds indicated with TH50, TH60, TH70, TH80 and TH120. The images are MRI images of the breast and the particular is related to an image region which could have a particular significance relatively to a suspected tumour lesion. As it appears clearly, at each recursive step within which a lower intensity threshold is determined and used for identifying objects the delimitation of regions becomes more difficult and the highlighted regions of the image identified by means of the seeding of the image with the thresholds are more and more spread all over the image and covers each one a very small area which is almost a dot so that no object can be delimited or individuated at lower thresholds.

The detection module provided according to the method of the present invention provides for a further step of extracting morphological features of the objects individuated in the image by the segmentation step.

Several different morphological features of the objects individuated in the image can be used and are currently known and used almost separately one from the other. Typical methods and algorithms for extracting morphological features of imaged objects are common knowledge, see for example Analyse von Gefäßstrukturen in medizinischen Schichtdatensätzen für die computergestützte Operationsplanung, Dissertation, Dirk Selle; Medizinische Bildverarbeitung, Heinz Handels, B. G. Teubner Stuttgart—Leipzig; Bildverarbeitung für die Medizin, Thomas Lehmann, Springer This known methods comprises image pattern recognition processes, edge detection algorithm and other similar algorithms.

Figure 8:
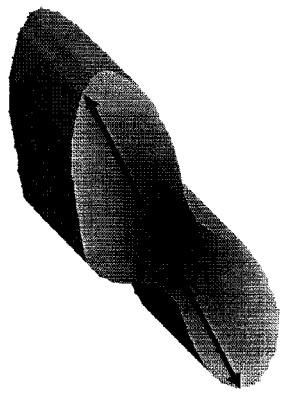
FIGS. 8 to 12 illustrates schematically examples of the criteria used in the method according to the present invention for carrying out the sorting out of image objects by means of the morphing step.

A first set of morphologic features of the objects in the image is represented in FIG. 8 and consists in the geometrical parameters of the object. Herein the object is represented by a three-dimensional body and the parameters measured are the volumetric size if the images are three dimensional images or the area if the images are two dimensional images. Further to this also the maximum diameter and the minimum diameter is determined out of the image of the objects. In the case of two dimensional images the two corresponding dimensions are determined i.e. maximum and minimum lengths.

Figure 9:
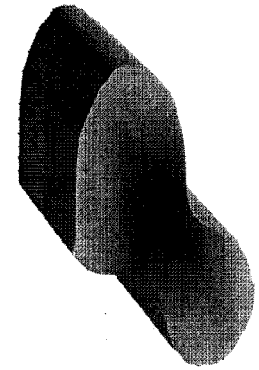

A further parameter for describing the morphology of the imaged object and which can be determined out of the image particularly a three dimensional image is the compactness. In this case the quotient between surface and volume can be determined and the fractal dimension of the image of the objects as indicated in FIG. 9.

Figure 10:
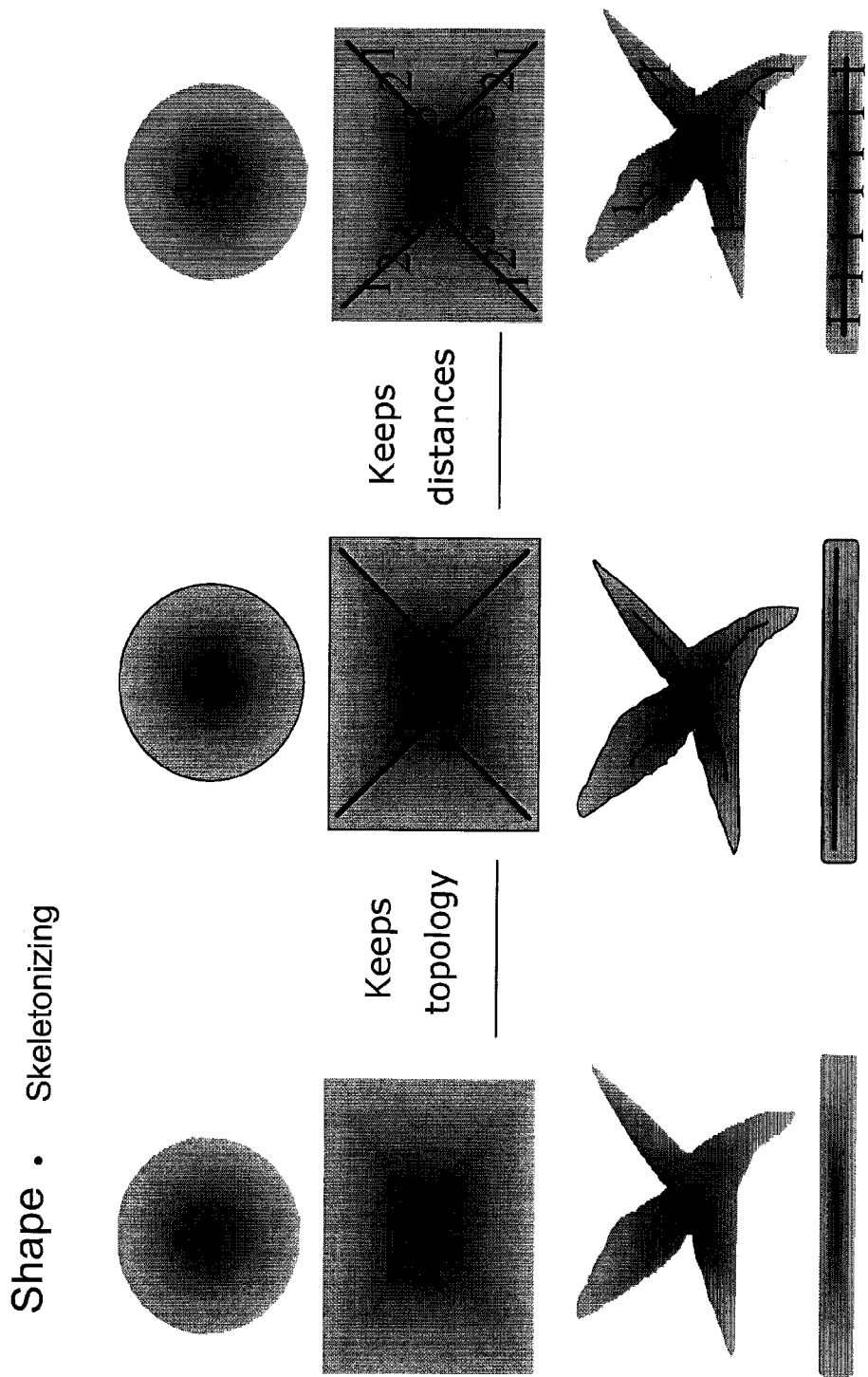
Figure 11:
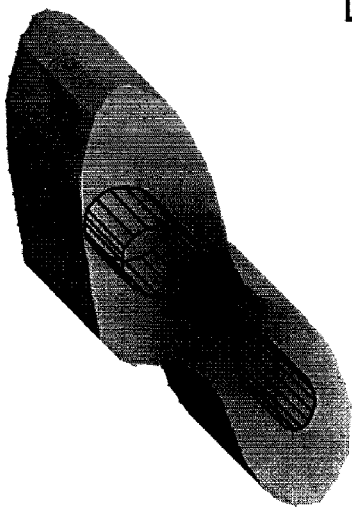

Still a further feature is the definition of the shape of the objects individuated in the image. In this case use is made of a known technique which is known with the denomination of skeletonizing of an image. Some examples of the skeletonizing process are illustrated in FIG. 10 relating to differently shaped objects as a dish, a rectangle an irregular cross like element and an elongated element. Skeletonizing allows to determine numerical parameters defining the shape and a more detailed description of this technique is disclosed in document Analyse von Gefäßstrukturen in medizinischen Schichtdatensätzen far die computergestützte Operationsplanung, Dissertation, Dirk Selle.

Figure 12:
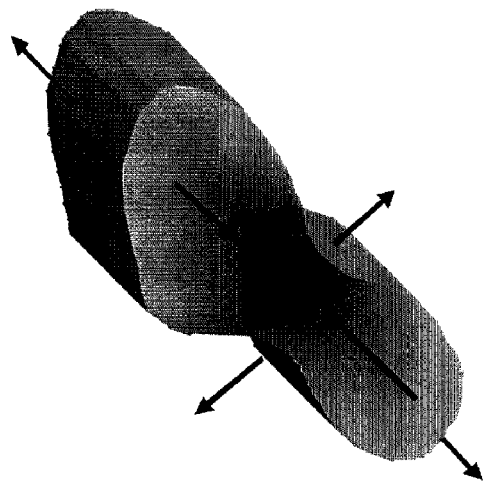

Still another parameter which can be determined relating to the morphological features of the objects individuated by the segmentation step in the images is the homogeneity. Numerical parameters describing this feature can be the average signal intensity within the image region corresponding to the object; Signal intensity deviation within the image region corresponding to the object and characteristics of the margins of the region of the image corresponding to the object as indicated in FIG. 12.

When imaging of a body in which contrast media are present is carried out further morphological parameters which can be sued are the size of the bubbles of the contrast media determined in $mm^3$ the number of bubbles in the image region corresponding to the object and the size of the biggest bubble expressed in $mm^3$.

Every one of this parameters describing with numerical values the objects of the image or at least parts of them are used for generating a vector for coding each object individuated in the image for further use as the input data of the evaluation module.

Relating to the dynamic features the present invention provides for a dynamic feature extraction subsystem which is used for evaluating a time dependent behaviour of the objects individuated in the image either due to spontaneous time dependent variations of the objects in the image or due to induced time dependent behaviours of the imaged object. A particularly relevant induced time dependent behaviour of imaged objects helpful in assessing tumour lesions is the determination of the contrast media perfusion behaviour of the objects. Perfusion measurement of contrast media uptake and washout behavior within the tissue of an imaged anatomical district for diagnostic purposes is a well known technique. This technique is based on the acquisition of a sequence of images of the same anatomical district taken at different time intervals. The first image is taken when no contrast media is present in the region to be imaged the other images are taken at different times after contrast media is provided in the region to be imaged. Contrast media is transported in the imaged region by means of the blood and lymphatic vessels. Thus the perfusion behaviour of contrast media can give indications on the vascularisation of the imaged region. Tumour lesions are normally connected by an increased vascularisation of the region where they are present due to the fact that the tumour tissue needs to be supplied for its growths. Thus the presence of an increased vascularisation can be an indication of the presence of a tumour lesion and this increase of vascularisation can be detected by means of the measurement of the signal intensity/time-curves.

The method according to the present invention comprises a susbsystem for dynamic features extraction for a sequence of images which consists in the measurement of parameters describing the contrast media perfusion behaviour of objects in the imaged region.

The measurement of the parameters describing the contrast media perfusion behaviour out of the above mentioned sequence of images comprises the steps of carrying out an image subtraction. This step is carried out typically after the images have been submitted to the registration step and eventually to the segmentation step.

Figure 13:
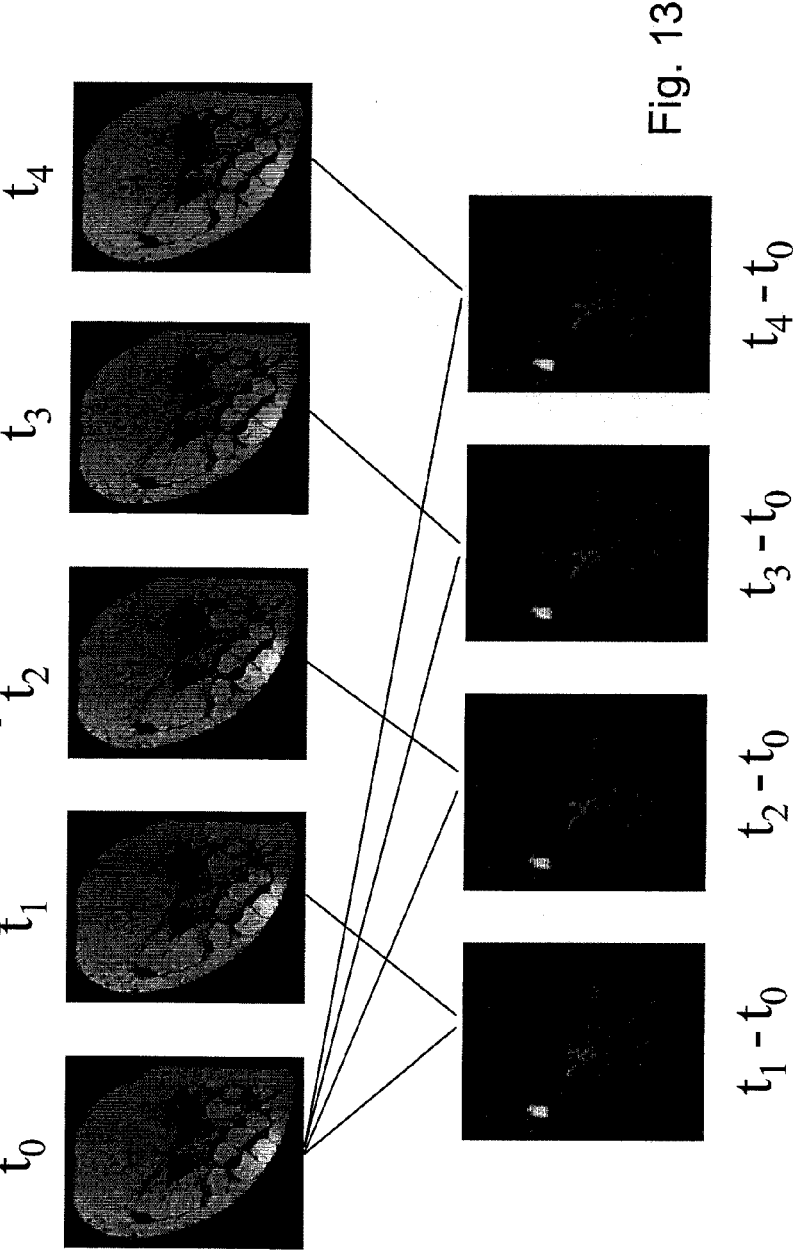
FIG. 13 illustrates schematically the step of extracting dynamic features of the imaged body by means of a sequence of images acquired at different times and in the presence of a contrast media in the imaged body.

FIG. 13 illustrates schematically the step of image subtraction for determining the contras agent uptake. The first row of images represents the sequence of images, particularly MRI images of the breast. The images of the sequence are taken at different times indicated by t0, t1, t2, t3, t4. Images taken at t0 correspond to a time instant where no contrast agent was present in the imaged region. Images taken at the following time instants are taken after a contrast agent was present in the imaged region.

The second row of images shows the result of image subtraction. The image taken at instant t0 taken when no contrast media was present is subtracted form each of the images taken at the instants t1, t2, t3, t4 when the contrast media is present in the imaged region. Each image in the second row is identified by the corresponding difference of time instants t1−t0, t2−t0, t3−t0, t4−t0.

Subtraction allows to widely eliminating image contributions which are not due to the contrast media, so that the mean intensity of each image resulting form the said subtraction step is essentially due to the contrast media.

The mean intensity of each image obtained by the said subtraction step is a numerical parameter which can be represented in relation to the time instant at which each of the images of the sequence has been taken. The graphic representation of the curve approximating the above parameters is illustrated in the intensity/time diagram on the left side of FIG. 15 and the curve is a so called signal intensity/time-curve which is a measure of the perfusion behaviour of the contrast media in the imaged region.

Figure 16:
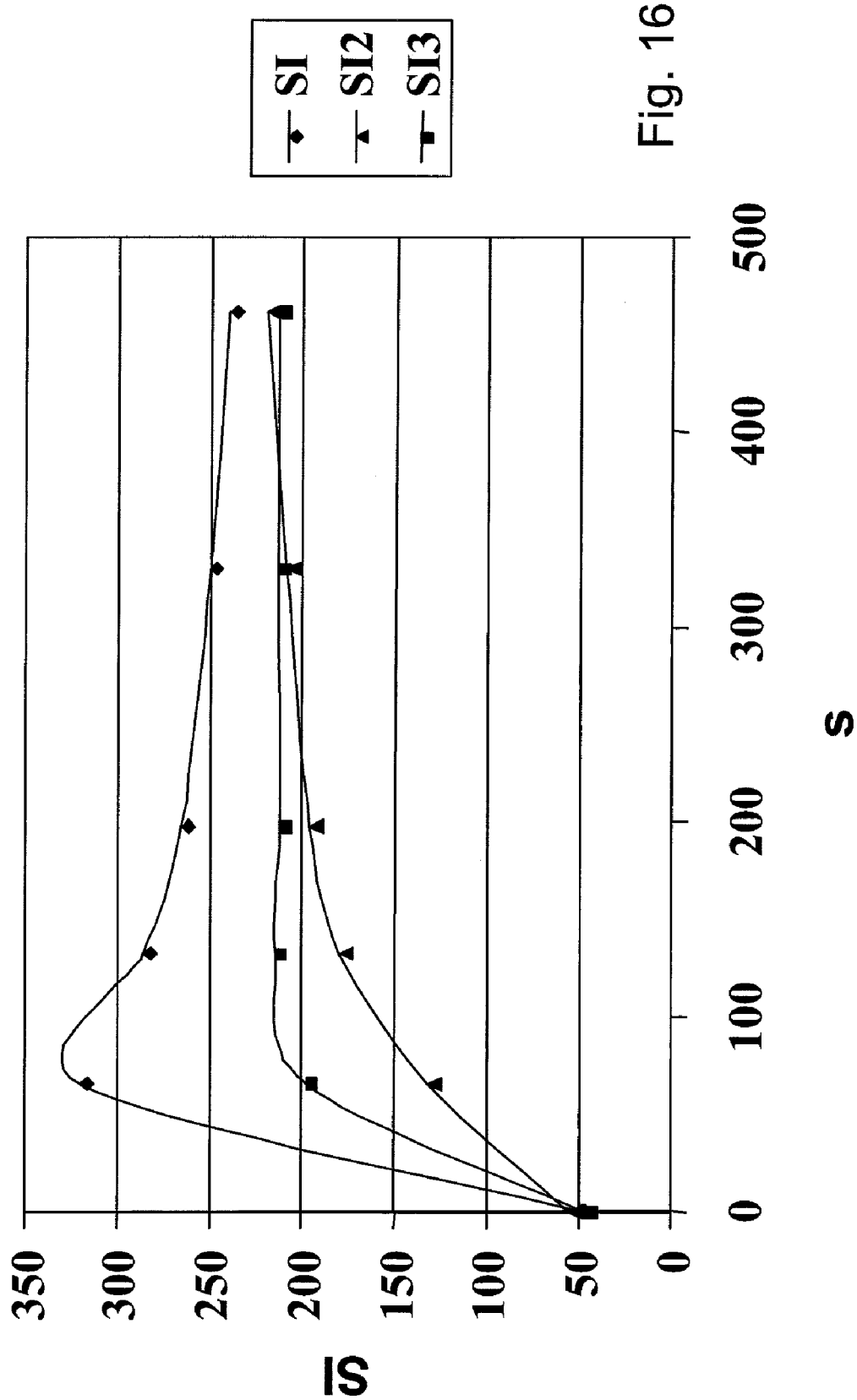
FIG. 16 is an example of a result of the different signal intensity/time-curves obtained for different objects in the image.

FIG. 16 illustrates in the same diagram three signal intensity/time-curves relative to three different cases.

It has to be noticed that if a segmentation step and an object individuation step is carried out on the images of the sequence, the perfusion behaviour in the form of the said signal intensity/time-curves can be carried out separately for each object individuated in the image so that the different signal intensity/time-curves of FIG. 16 can also represent the signal intensity/time-curves of three different objects individuated by segmentation and object extraction in the sequence of images, thus giving information of the perfusion behaviour of each object.

The results of the signal intensity/time-measurements can be used for generating further parameters which are calculated as a function of this information.

Figure 15:
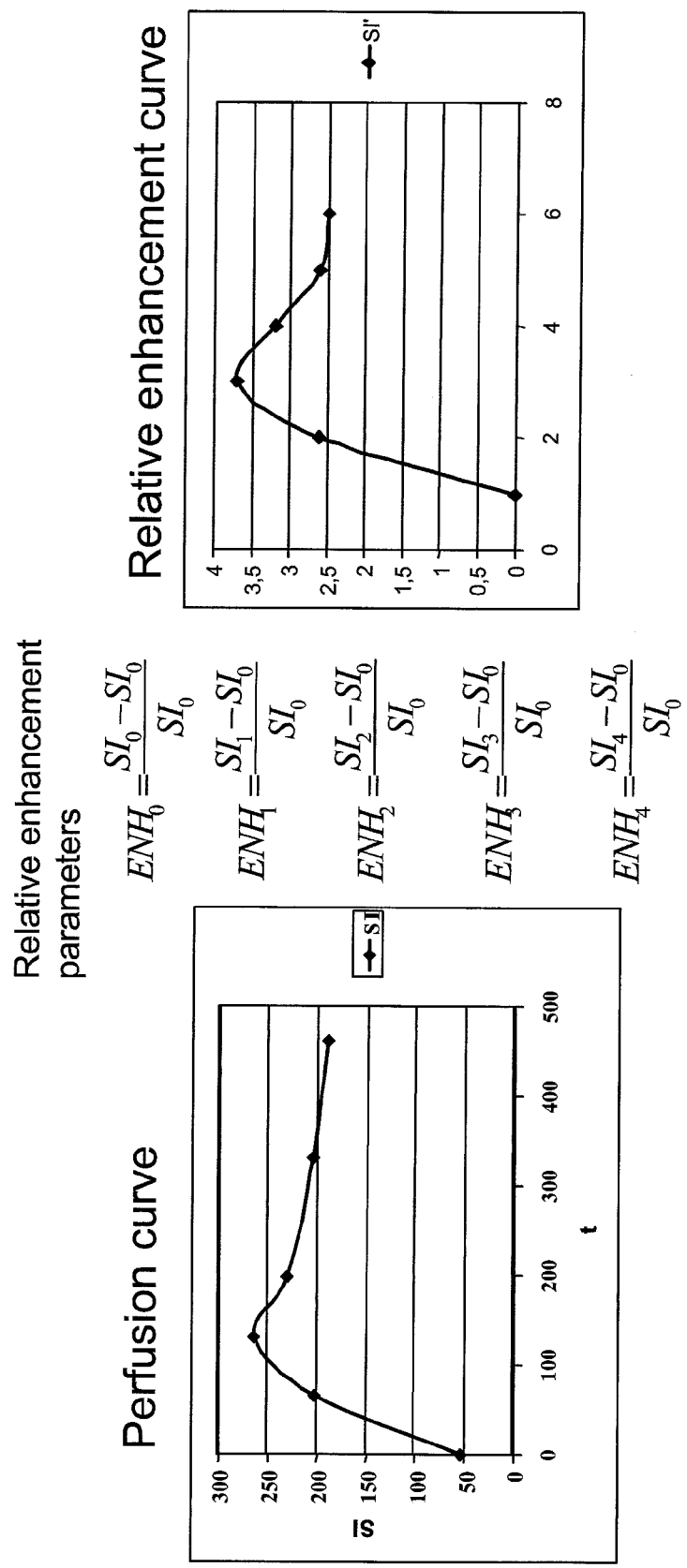
FIG. 15 illustrates a so called signal intensity/time-curve and a choice of parameters determined according to the table of FIG. 14 by means of the said signal intensity/time-curve.

In FIG. 14 a table is provided summarising some of the principal parameters which can be calculated by means of the perfusion measurement step. Particularly relevant are the so called relative enhancement parameters indicated by $ENH_n$, with n=1, 2, 3, 4, 5. In the table a sequence of six images is considered taken a different time $t_n$ with n=1, 2, 3, 4, 5. FIG. 15 illustrates graphically the enhancement parameter curve which passes through the points defined by the enhancement parameters and resulting from the signal intensity/time-curve which is depicted on the left side of the FIG. 15.

Figure 17:
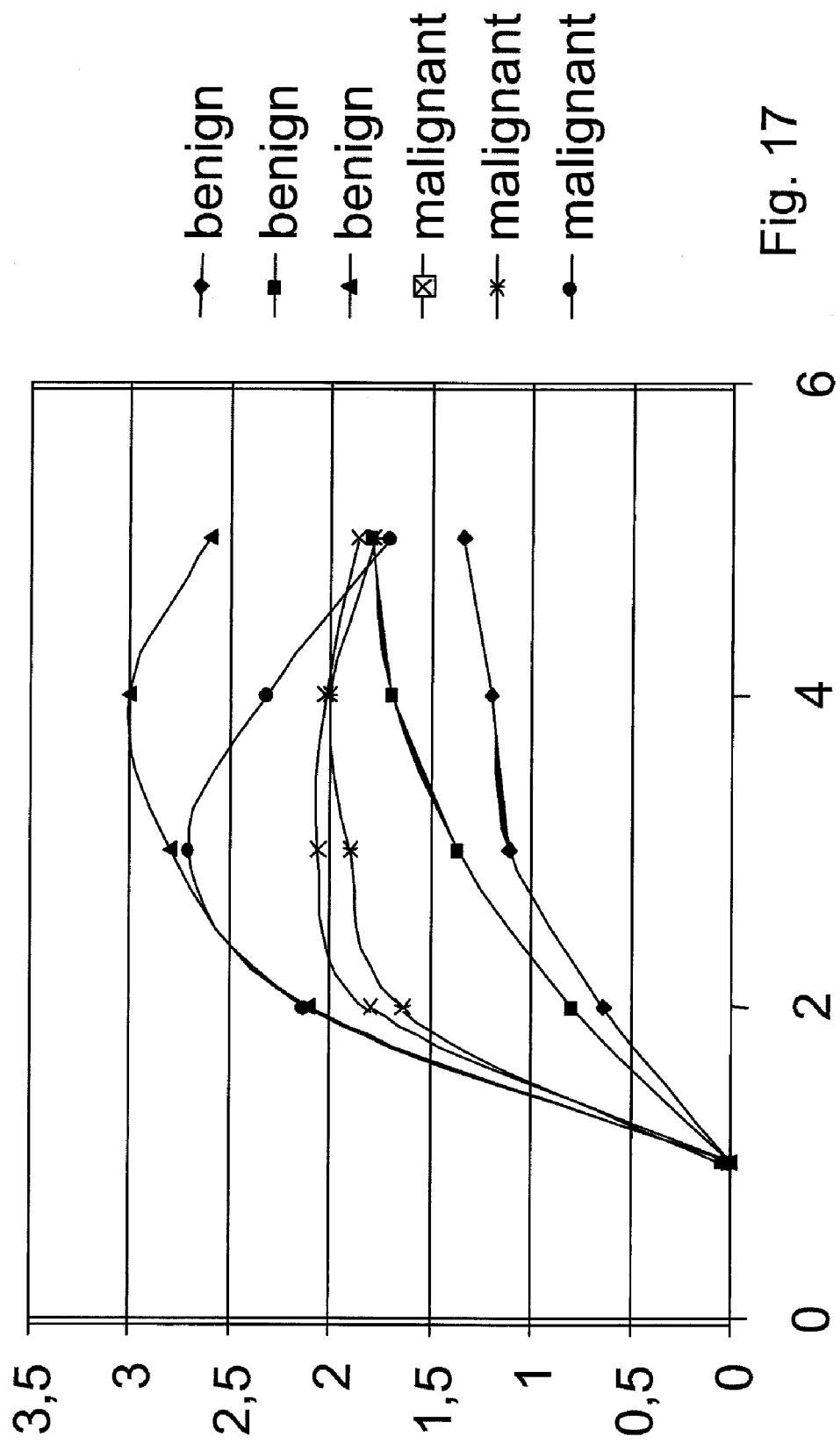
FIG. 17 is an example of the different parameters determined from the signal intensity/time-curves of different objects in an image according to the example of FIG. 15 and their correspondence with a benign or malignant tumour lesion determined by comparing the said curves with the typical behaviour of such lesions relatively to contrast media perfusion.

FIG. 17 illustrate the relative enhancement curves relating to different cases or to different objects in an image. The shape of the relative enhancement curves gives an indication about the fact if the imaged object or the imaged case can be considered as a benign tumour tissue or as a malignant tumour tissue.

According to the table of FIG. 14 further parameters can be determined by means of the enhancement parameters which defines the shape of the enhancement curves and so parameters for indicating if the perfusion behaviour of the imaged object can be considered similar to the one expected for a tumour lesion and if this tumour lesion is benign or malignant.

Particular further parameters for describing numerically the enhancement curve shapes or features are: the peak value among each enhancement parameter ENHmax; The peak value among the two first enhancement parameters ENHalt; The relative signal increase between the first and the second post-contrast measurement ENH1-2; The maximum slope determined as the relative signal increase from the condition of absence of contrast media to the condition of presence of contrast media at the time the first image is taken of from this first image to the following one which ever value is higher and defined as MSLP; the saturation SAT which is calculated as the signal intensity reached during the first image of the sequence taken when the contrast media is present with respect to the peak signal intensity reached in the sequence of images taken when contrast media is present in the imaged region; a first washout parameter ENH2-5 indicating the change of signal intensity from the second image to the last (inn this example the fifth) image taken when contrast media is present in the imaged region; a second washout parameter ENH3-5 indicating the change of signal intensity from the third image to the last (in this example the fifth) image taken when contrast media is present in the imaged region. Obviously the number of washout parameters depends on the number of enhancement parameters and thus from the number of images of the sequence.

The method and system of the present invention provides for a decisional algorithm which sets a first decision whether certain object or zones of the image can be considered as being potential lesions or not. The decision is based on the combination of the result of the morphological and dynamical features extracted in the previous steps. The algorithm for describing the morphology of the lesion works on the results of the segmentation and the image volume information and takes also the T2 weighted images into account. A list of shape and appearance of the segmented lesions is generated by a collection of the above disclosed different image processing methods:

Morphology Shape

Skeletonizing: By the use of a topology conserving Skeletonizing the lesion object are represented in a more simple form. Statistic evaluations draw conclusions from the lesions shape (e.g. round, flat, spiculated). Information of size of the skeleton and its distance to the boundary are used.

Encapsulated bubbles are detected as measure for necroses. The idea of connectivity component is used.

Voxel counting: simple description of volume size, max. and min. diameter, boundary size are calculated by voxel counting. Compactness values are given by fractal dimension, ratio of boundary size to volume size or average distance to centre point.

water ratio: the detected lesion is overlaid by coordinate transformation to the T2 weighted image. By thresholding the water inclosed are is determined.

Morphology Dynamic

In addition to the morphology also dynamic feature are calculated:

Dynamic curve of whole lesion: The average intensity value of a lesion in all time frames is calculated. The frequency of the dynamic curve is normalised to time frame zero, also the time intervals are normalised.

Dynamic curve of hotspot: The same procedure of the whole lesion is repeated for the location with the maximum intensity. This hotspot has to lie within the lesion in all time frames.

Shape of lesion boundary: First the average intensity on the boundary of a lesion object is determined. Twice the lesion is expanded by a dilation function and the calculation of the boundary is repeated.

In order to allow comparison and the decisional step, all morphological values are normalised, so they are independent to the voxel resolution, image size, time frames of MR protocol and used contrast media. If useful the values are scaled to a fix range.

At least two of these parameters are directly used to eliminate the high number of false positive lesion findings.

The parameters describing the dynamic features which has been extracted as disclosed above, all of them or a part of them, is used as numeric data for completing the vectors for coding each object individuated in the image as described above and which is destined to be the input data of the evaluation module.

Vector coding of the processed image data can be carried out object by object or event pixel or voxel by voxel. In this case morphology information and dynamic features information will be the same for the pixels or voxels which are within the image area corresponding to an object individuated in the image.

The vector for coding the image data processed by the detection module and the subsystem for extracting the dynamic features can be further competed as disclosed at the beginning of the description with further data relating to the patient history and to other personal data of the patient.

According to a further feature of the present method the vector for coding the image data to be further processed by the evaluation module can also comprise also the parameters describing the aspect of each pixel or voxel as well as the aspect of a certain number of pixels or voxels of a predetermined surrounding of each pixel or voxel to be coded as well as further characteristic parameters which can be determined as characteristic mathematical parameters of the image data treated as a matrix.

Relating to the evaluation module the method according to the present invention provides that this module processes the above defined image data by means of a classification algorithm such as a predictive algorithm or as a clustering algorithm.

As a predictive algorithm it is possible to use a so called Artificial Neural Network or similar mathematical non linear structures. The clustering and/or the Artificial Neural Network as well as any other predictive or classification algorithm are trained by means of a database of images of known cases in which the parameters provided in the vectors for coding the image according to the previously described structure are univocally associated to the searched features or qualities of the imaged objects in the images. The database of known cases has to be constructed keeping in mind that the images has to be processed in an analogous way as the images of the unknown cases. Training, testing and generally using such predictive or classification algorithms are known steps for the skilled person.

The presence of the features or qualities is parameterised by defining certain variables whose values are set as indicating presence of the searched features or qualities.

In the present example where tumour lesions and further their quality of benign or malignant has to be determined in the imaged region, two variables can be used for defining the presence of tumour lesions and for defining the quality of benign and malignant each of which variable can take one of the two values 0 or 1.

Figure 18:
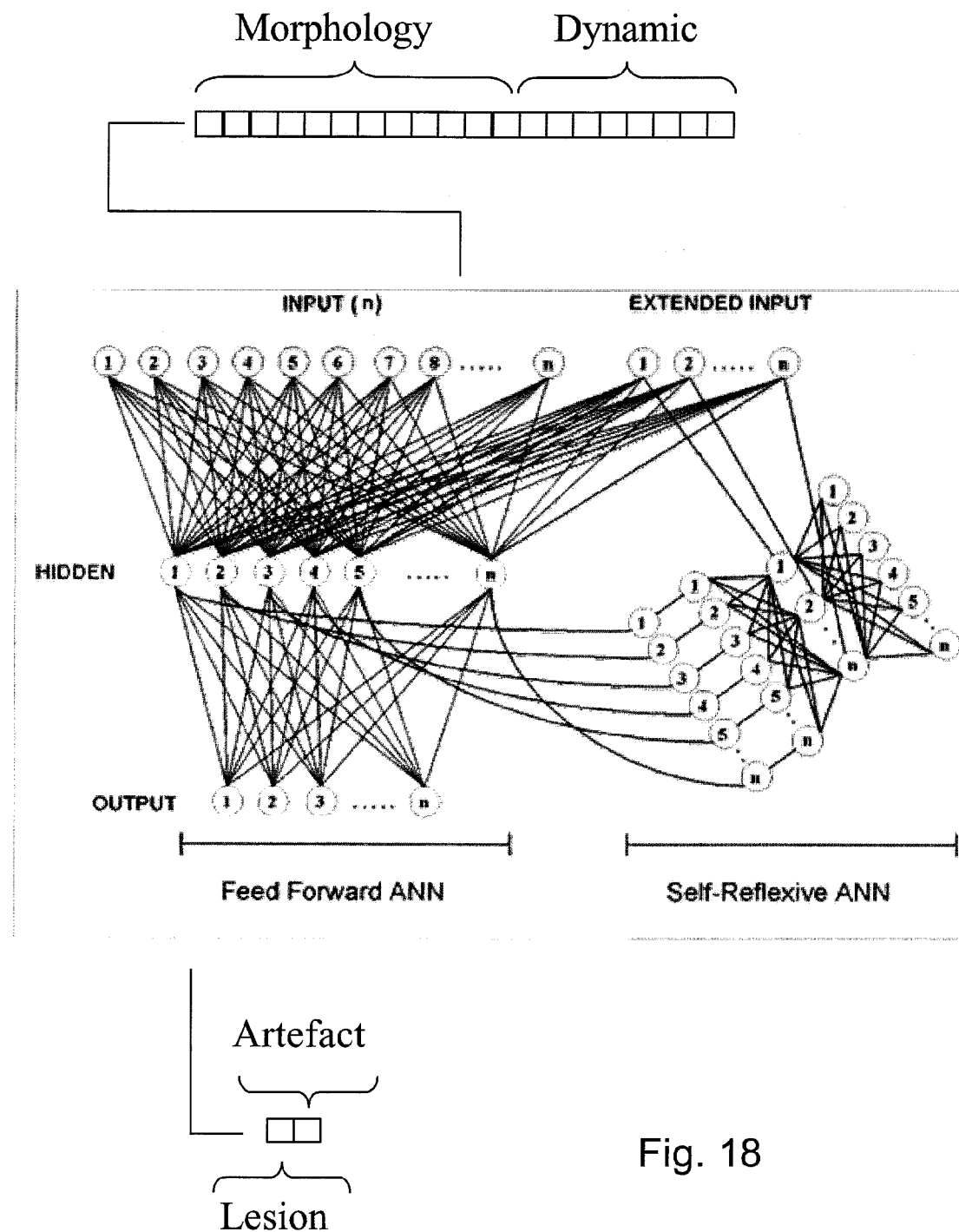
FIG. 18 illustrates a simplified diagram representing an example of a first classification process which is specialised in classifying pixels of an image relating to the correspondence of the said pixels with a first feature or quality in particular relating to the fact that the pixel in the image represents a tumour lesion or an artefact.
Figure 19:
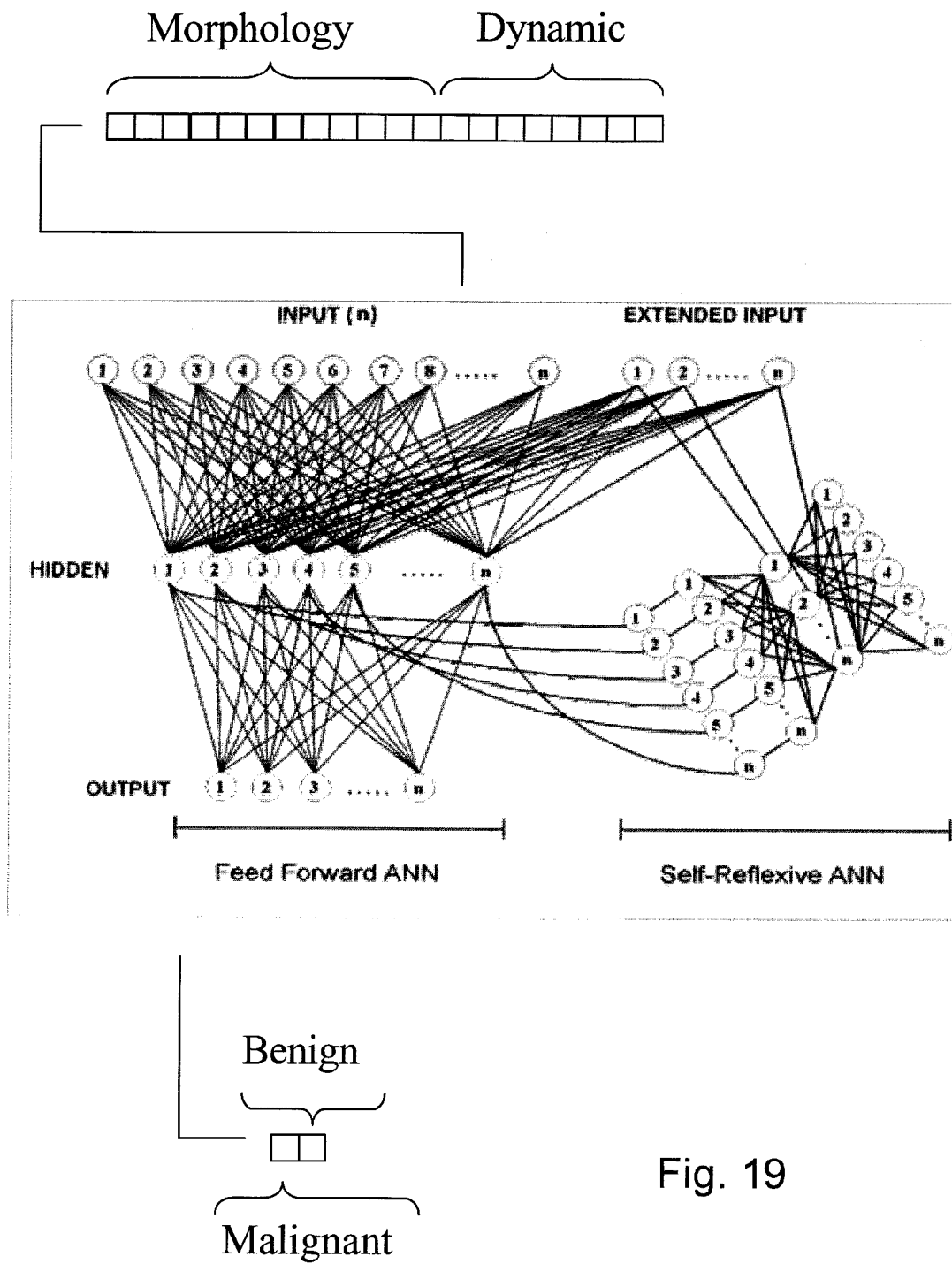
FIG. 19 is a diagram according to FIG. 18 where a second classification process is shown by which pixels of an image are classified relating to the correspondence of the said pixels with a second feature or quality in particular relating to the fact that the pixel in the image represents a benign or a malignant tumour lesion.

As indicated by FIGS. 18 and 19 the evaluation module can comprise two or more classification algorithms each one specifically trained for predicting the presence or absence of a certain feature or quality.

In the present case a first Artificial Neural Network is specifically trained and tested for determining the presence or absence of a tumour lesion, while a second Artificial Neural Network is specifically trained and tested for determining if such lesions are benign or malignant. In such case the two algorithms are connected n a cascade of algorithms.

When the searched features or qualities are more than the two of the present example, than it is possible to provide specifically trained classification algorithms such as artificial neural networks destined to determine the presence and absence of each of the searched features independently.

As a further feature of the present method for processing and evaluating images, particularly diagnostic images, for each of the processing modules such as the detection module and the subsystem for extracting dynamic features and where possible for each of the processing steps carried out by each processing module or subsystem the modified image data and the parameters determined can be visualized in order to allow a visualisation of the partial results.

The final classification result is printed out or visualized on a monitor by printing alphanumeric information and also images. In the images the pixels or voxels relating to the objects in the said images for which the searched feature has been found to be present are highlighted relatively to the other pixels or voxels of the image for example by giving them a coloured aspect while the rest of the image is kept as a greyscale image.

According to a further feature of the present invention a particular way of representing the pixels of the image which has been classified as corresponding to imaged objects having a searched feature or quality is provided.

Referring to the present example the classification module comprises two different classification steps carried out each one by a dedicated specifically trained artificial neural network. The presence/absence of each searched feature is parameterized by means of two output variables which can assume both the two values "0" or "1". The presence of the searched feature or quality is determined by the artificial neural network is defined as the pair of values "1,1" for the output variables. Absence of the searched feature or quality by the value pair "0,0" for the two output variables. The pair of values "1,0" and "0,1" are thus indefinite cases.

Currently an aspect of the pixel or voxel is defined for the case that the pixel or voxel corresponds to an image of an object which the artificial neural network has classified as having the searched feature or quality.

In the present case the output values of the artificial neural network are used to define a parameter for describing the pixel or voxel appearance in a colour space according to one colour model.

Different kinds of colour models can be used. There is a particular colour model which is specifically suited for describing the appearance of pixels for monitors or the like and this is the so called RGB colour model. In this case the appearance of the pixels is defined by three variables, namely R, G, B which stands for red, green and blue. For more details see for example the on-line encyclopaedia called Wikipedia at the pages http://en.wikipedia.org/wiki/Color_theory and http://en.wikipedia.org/wiki/Color_space and corresponding links According to the said feature of the present invention, one first output variable of the two output variables of the artificial Neural Network determines the value of one of the parameters defining the pixel appearance according to the chosen colour model, while the second output variable is used for determining the second parameter of the chosen colour model. Generally the colour models defines the aspect of the pixels by means of at least three or even four parameters. So in this case the third parameter or eventually the fourth parameter depending on the model that has been chosen is or are set to a zero value or are defined by a combination of the two output variables of the artificial neural network.

Obviously when the classification or prediction algorithm has more than two output variables, the values of these variables can be used either separately for each variable or in a combination of some or all the said output variables for determining the parameters of the chosen colour model.

In the present case of the example shown, the classification module is formed by two artificial neural networks which are dedicated each one respectively for classifying the pixels of the image as being related to regions of the imaged body that have or do not have one of two searched features. The two specific features are "tumour lesion" and "benign or malignant". Each artificial neural network determining the presence or the absence of one of the two features has an output layer comprising two output knots. The values which each knot can assume being defined in a space comprising the discrete numerical values "0" and "1". In this case it is possible to use a variant of the above described way of determining one or more parameters of the colour model chosen for giving to the pixels of the image a certain appearance. A first parameter can be determined by a combination or any other function of the two output values of the first artificial neural network, while the second parameter by a combination or any other function of the two output values of the second artificial neural network.

Relating to the third and eventually to the fourth parameter depending on the colour model that has been chosen for representing the pixel these can be set to predefined fixed values or be determined as combinations or functions of the output variables of both the artificial neural network.

Other parameters or numerical values can be used for determining one of the parameters of the colour model such as for example the fitness score of the classification results or other statistical meaningful parameters.

According to the above feature the classification results in the image can be represented in a visual graphical way and in the image each result is indicated including the cases where the two values of the output variables do not have a precise meaning relating to the classification.

Generalizing, the above improvement can be defined as follows:

Let the artificial neural network ANN be a ANN trained on a DB. Once the artificial neural network ANN receives an unknown input vector v_i then it generates a fuzzy output on each of the 'n' output nodes where n=1, 2, . . . .

For the purpose of displaying this information each output node is assigned to an image characteristics as defined by a parameter of a colour model such as the RGB values, or the HUE values or other combinations.

In the case that only an output node is provided, the output values of this node is typically displayed with 2 colors, for instance if the output value out_value>threshold then it's RED, while it is GREEN otherwise. The fuzziness of the output can be used by using out_value in the RGB color coding. For instance, if 0<out_value<0.33 then RGB=(0,0, out_value*255*3) if 0.33<out_value<0.66 then RGB=(0, out_value*255*2,0) if 0<out_value<0.33 then RGB=(out-_value*255,0,0)

For an artificial neural network ANN with two output 2 nodes the parameters of a colour model, for instance an RGB colour model, the values of the parameters of the RGB model could be set as an example according to the following expression:

$$R,G,B=(out\_value\_1*255,(out\_value\_1-outvalue\_2)*255,out\_value\ 2),$$

or similar combinations

To combine more than three nodes and colour mapping see, http://en.wikipedia.org/wiki/Color_theory http://en.wikipedia.org/wiki/Color_space When the classification module is formed by a cascade of artificial neural network, it is possible to use the output of each of these artificial neural networks to define the appearance of the pixels or voxels in the image according to the following function for determining the parameters: R,G,B= (out_value_NN1, out_value_NN2, 0).

Referring to FIG. 20 an example of the output of the processing and evaluation method according to the present invention is shown. The example of FIG. 2 is a combination of information in alphanumeric form and in graphical form.

Alphanumeric information comprises information about the relevant data describing the kind of image acquisition used.

Furthermore alphanumeric information comprises data about the number of objects classified as having the searched features which has been determined by the image processing, the number of the said objects which ha other relevant features, the relevant parameters describing morphology of the objects and dynamic features of the objects, the statistical probability that the classification results are true and the possible probability that the classification results are not true and due to an error.

Graphical information comprises an overview image of the entire imaged region and the enlarged particulars of the image relatively to the objects individuated in the image and having the searched features. When dynamic features are determined also a graphic representation of the function approximating the time dependent behaviour of at least a relevant parameter describing this time dependent behaviour and in the present example the so called signal intensity/time-curve.

Relatively to the image processing and evaluation method it has to be stressed out that due to image preparation particularly comprising the step of segmentation and object extraction, the image evaluation module can be applied in a traditional way analysing the image pixel by pixel or voxel by voxel or analysing the image object by object. So in order to provide a classification or prediction of the presence/absence of the searched feature for each object the evaluation module considers the objects individuated in the image by segmentation as unitary elements. The features of the image of the object are parameterized numerically by means of the determination of morphological features form the image of the object and by dynamic features consisting in a certain specific time dependent behaviour of the object under certain conditions.

Thus the data base of known cases has records each one of these records being referred to an object the features or qualities of which objects are known and the image of the said objects being processed according to the detection module and eventually also to the subsystem for extracting dynamic features as disclosed above

The invention claimed is:

1. A method for automatic processing and evaluation of an image comprising:
   processing image data of a digital input image of an imaged body with an image processing tool comprising a software program which is embodied in a non-transitory computer readable storage medium and executable by computer hardware; and
   generating, with the image processing tool, a modified digital output image having image data outputted in a graphical and/or alphanumerical format highlighting a predetermined feature or quality of a region of the imaged body,
   wherein the image processing tool further comprises,
      an image detection module including a first image processing module based on a non expert image processing algorithm, the image detecting module outputting a modified image file, and
      a classification or evaluation module processing modified image data in the modified image file, the classification or evaluation module including a second image processing module that includes an image processing element comprising an expert image processing algorithm, an output of the expert image processing algorithm being a further modified image file, in which pixels or voxels are highlighted corresponding to an imaged object having the predetermined feature or quality,
   wherein the image detection module further comprises a subsystem for extracting dynamic features of the imaged body by measuring time dependent parameters describing a spontaneous or induced time dependent behavior of the imaged body,
   wherein the subsystem for extracting dynamic features measures a perfusion behavior of a contrast agent in tissues of the imaged body by using a time dependent signal intensity/time curve,
   wherein the detection module analyzes the input image to identify groups or clusters of pixels or voxels having similar parameters defining their appearance, and wherein the detection module further defines said groups or clusters of pixels or voxels as one or more images of one or more unitary objects in the image, thereby providing an indication of a target object in the imaged body,
   wherein the one or more unitary object in the one or more images determined by a segmentation processing step of the image,
   wherein the image detection module further provides a measurement step of numeric parameters describing one or more morphological features of the one or more unitary objects in the image,
   wherein the detection module performs a comparison step of the numeric parameters describing the one or more morphological features of the one or more unitary objects in the one or more images with nominal reference parameters describing morphological features of searched features or qualities of the imaged body or of searched objects in the imaged body, and a selection step determining a subset of a valid unitary object in the one more unitary objects in the one or more images based on results of the comparison step,
   wherein the numeric parameters of the one or more morphological features are measured and subjected to comparison with nominal values related to dimensions and proportions of the one or more unitary objects in the image,
   wherein the nominal values relate to a shape of the one or more unitary objects, and
   wherein the shape of the one or more unitary objects is parameterized by having the images of the one or more unitary objects undergo a skeletonization process.

2. The method according to claim 1, wherein the numeric parameters of the one or more morphological features are measured and subjected to comparison with the nominal values to determine compactness of the one or more unitary objects and, when a three dimensional image is being processed, a quotient surface/volume and a fractal dimension.

3. The method according to claim 1, wherein the digital input image is acquired in the presence of a contrast medium in the imaged body, and wherein the parameters of the one or more morphological features are measured and subjected to comparison with nominal values related to size of contrast media voids in the one or more unitary objects, to a number of contrast media voids in the one or more unitary objects, and to a size of the biggest contrast media void in the one or more unitary objects.

4. The method according to claim 1, wherein the parameters describing the one or more morphologic features are measured and subjected to comparison with nominal values related to homogeneity of the one or more unitary objects and comprise an average signal intensity of the groups or clusters of pixels or voxels falling within the images of the one or more unitary objects, a signal intensity standard deviation of the pixels or voxels falling within the images of the one or more unitary objects, and properties of margins of the images of the one or more unitary objects in the image.

5. The method according to claim 1, wherein the subsystem for extracting dynamic features performs the following steps:
   acquiring a sequence of images of the imaged body, each of the said images being acquired at different time instants;
   comparing images in the sequence of images with one or more parameters providing a time dependent behavior of the imaged object;
   determining a time dependent intensity variation curve by including a difference in mean intensities of the images in the sequence of images, thereby developing a time dependent intensity curve; and determining values of parameters describing analytical or geometrical features of the time dependent intensity curve, thereby providing dynamic features of the imaged body.

6. The method according to claim 5, wherein the time dependent behavior is related to the perfusion of a contrast medium, a first image of the sequence of images being acquired before the contrast medium is present in the imaged body and following images in the sequence of images being taken at different time instants after the contrast medium is present in the imaged body.

7. The method according to claim 6, wherein comparing images comprises subtracting the first image of the sequence of images from each of the following images of the sequence of images, thereby causing the time dependent intensity variation curve to be a perfusion curve.

8. The method according to claim 5, wherein the dynamic features of the imaged body are analytical or some geometrical descriptor parameters describing the signal intensity/time curve.

9. The method according to claim 5, wherein the subsystem for extracting dynamic features comprises a registration step registering the images of the sequence of images one with respect to the other.

10. The method according to claim 9, wherein the subsystem for extracting dynamic features comprises a segmentation and object individuation step after the registration step, the segmentation and object individuation step identifying unitary objects in the one or more images corresponding to unitary objects in the imaged body, the registration and the segmentation and object individuation steps being carried out independently for each unitary object in the image.

11. A method for automatic processing and evaluation of an image comprising:
   processing image data of a digital input image of an imaged body with an image processing tool comprising a software program which is embodied in a non-transitory computer readable storage medium and executable by computer hardware; and
   generating, with the image processing tool, a modified digital output image having image data outputted in a graphical and/or alphanumerical format highlighting a predetermined feature or quality of a region of the imaged body,
   wherein the image processing tool further comprises,
      an image detection module including a first image processing module based on a non expert image processing algorithm, the image detecting module outputting a modified image file, and
      a classification or evaluation module processing modified image data in the modified image file, the classification or evaluation module including a second image processing module that includes an image processing element comprising an expert image processing algorithm, an output of the expert image processing algorithm being a further modified image file, in which pixels or voxels are highlighted corresponding to an imaged object having the predetermined feature or quality,
   wherein the image detection module further comprises a subsystem for extracting dynamic features of the imaged body by measuring time dependent parameters describing a spontaneous or induced time dependent behavior of the imaged body,
   wherein the subsystem for extracting dynamic features performs an object selection step that includes selecting valid unitary objects by comparing parameters describing morphological features of the unitary objects in the image with nominal reference parameters describing morphological features of searched features of the imaged body or of searched objects in the imaged body, and
   wherein the object selection step is carried out before or after extracting the dynamic features of the valid unitary objects, thereby causing non valid unitary objects not to be submitted to the dynamic feature extraction or causing objects, for which the dynamic feature extraction has been carried out, to be considered non valid and ignored.

12. The method according to claim 11, wherein the object selection step further comprises providing a measurement step of numeric parameters describing the morphological features of the one or more unitary objects in the image.

13. The method according to claim 11, wherein the classification or evaluation module carries out an object based classification by considering one or more parameters describing morphological features of the imaged object and dynamic features related to the imaged object.

14. The method according to claim 13, wherein the imaged object identified in the image is coded by a vector comprising as components the one or more parameters describing the morphological features of the imaged object and the dynamic features of the imaged object.

15. The method according to claim 13, wherein input data of the classification or evaluation module comprises vectors, each pixel or voxel in the image being coded by a vector comprising as components parameters describing an appearance of the pixel or voxel, parameters describing an appearance of a number of surrounding pixels or voxels, and, when the pixel or voxel falls within the imaged object, the one or more parameters describing the morphological and dynamic features of the imaged object.

16. The method according to claim 15, wherein the vector further comprises as components parameters describing mathematical features of a matrix of the parameters describing the appearance of the pixel or voxel and of the number of surrounding pixels or voxels.

17. The method according to claim 15,
   wherein an output of the classification or evaluation module is parameterized by n-tuples of output variables having a predetermined value range,
   wherein a presence or absence of a searched feature or quality or of a searched object in the imaged body is univocally associated to a predetermined combination of values of the n-tuples of output variables falling within the predetermined value range, and
   wherein an image region and/or each pixel or voxel of the imaged object is represented in a modified output image by a specific appearance, which is defined by parameters of a color model describing a color space, the parameters of the color model being determined as a function of the values of the n-tuples of output variables.

18. The method according to claim 17, wherein, for determining the presence of more than one searched feature or quality or of more than one kind of searched object in the imaged body, the classification or evaluation module comprises a classification algorithm, which is specifically trained for independently recognizing or predicting the presence of the searched feature or quality, of part of the searched feature or quality, or of one or part of one kind of the imaged object.

19. The method according to claim 18,
   wherein, for determining the presence of the more than one searched feature or quality or of the more than one kind of searched object in the imaged body, a first feature or quality or a first kind of the imaged object is further identified by at least two different additional features or qualities or by subclasses of kinds of imaged objects, and wherein the classification algorithm is specifically trained for independently recognizing or predicting a presence of the more than one or part of the more than one searched feature or quality, or of the more than one or part of the more than one kind of searched object, output data of a first classification algorithm being further used as input data of a second classification algorithm by adding the output data of the first classification algorithm to the vector coding each pixel or voxel or the imaged object in the image.

20. The method according to claim 19, wherein the output of the classification or evaluation module is provided in a modified image, the modified image having image regions and/or each pixel or voxel represented through a specific appearance, wherein the specific appearance is defined by the parameters of the color model describing the color space, and wherein each or part of the parameters of the color model is determined as the function of values of the n-tuples of output variables of only one or more of the first and the second classification algorithms.

21. The method according to claim 19, wherein the first and the second classification algorithms are trained through a database of known cases, the database comprising one or more known images for each known case, the one or more known images being processed for identifying objects coded by a vector having parameters that describe morphological features of objects in the known images and dynamic features, the morphologic parameters and the dynamic features of the objects in the known images being determined according to one or more of the step of claim 1 and being parameterized with numeric variables.

22. The method according to claim 19, wherein at least one of the first or the second classification algorithms is an artificial neural network.

23. A system for automatic processing and evaluation of images comprising:

a software program embodied in a non-transitory computer readable storage medium and executable by computer hardware, the software program being configured for performing the following steps:

processing image data of a digital input image of an imaged body with an image processing tool comprising a software program which is executable by computer hardware; and generating, with the image processing tool, a modified digital output image having image data outputted in a graphical and/or alphanumerical format highlighting a predetermined feature or quality of a region of the imaged body, wherein the image processing tool further comprises, an image detection module including a first image processing module based on a non expert image processing algorithm, the image detecting module outputting a modified image file, and a classification or evaluation module processing modified image data in the modified image file, the classification or evaluation module including a second image processing module that includes an image processing element comprising an expert image processing algorithm, an output of the expert image processing algorithm being a further modified image file, in which pixels or voxels are highlighted corresponding to an imaged object having the predetermined feature or quality, wherein the image detection module further comprises a subsystem for extracting dynamic features of the imaged body by measuring time dependent parameters describing a spontaneous or induced time dependent behavior of the imaged body, wherein the subsystem for extracting dynamic features measures a perfusion behavior of a contrast agent in tissues of the imaged body by using a time dependent signal intensity/time curve, wherein the detection module analyzes the input image to identify groups or clusters of pixels or voxels having similar parameters defining their appearance, and wherein the detection module further defines said groups or clusters of pixels or voxels as one or more images of one or more unitary objects in the image, thereby providing an indication of a target object in the imaged body, wherein the one or more unitary object in the one or more images determined by a segmentation processing step of the image, wherein the image detection module further provides a measurement step of numeric parameters describing one or more morphological features of the one or more unitary objects in the image, wherein the detection module performs a comparison step of the numeric parameters describing the one or more morphological features of the one or more unitary objects in the one or more images with nominal reference parameters describing morphological features of searched features or qualities of the imaged body or of searched objects in the imaged body, and a selection step determining a subset of a valid unitary object in the one more unitary objects in the one or more images based on results of the comparison step, wherein the numeric parameters of the one or more morphological features are measured and subjected to comparison with nominal values related to dimensions and proportions of the one or more unitary objects in the image, wherein the nominal values relate to a shape of the one or more unitary objects, and wherein the shape of the one or more unitary objects is parameterized by having the images of the one or more unitary objects undergo a skeletonization process.

24. The system of claim 23, wherein the software program comprises instructions having code lines that are saved on a portable machine-readable storage medium.

* * * * *